United States Patent
Hildebrand et al.

(10) Patent No.: US 11,181,532 B2
(45) Date of Patent: Nov. 23, 2021

(54) DELTA-LIKE LIGAND 1 FOR DIAGNOSING SEVERE INFECTIONS

(71) Applicant: Universität Heidelberg, Heidelberg (DE)

(72) Inventors: Dagmar Hildebrand, Dossenheim (DE); Klaus Heeg, Heidelberg (DE); Florian Uhle, Heidelberg (DE); Markus Weigand, Wettenberg (DE)

(73) Assignee: UNIVERSITÄT HEIDELBERG, Heidelberg (DE)

( * ) Notice: Subject to any disclaimer, the term of this patent is extended or adjusted under 35 U.S.C. 154(b) by 0 days.

(21) Appl. No.: 16/757,003

(22) PCT Filed: Oct. 25, 2018

(86) PCT No.: PCT/EP2018/079273
§ 371 (c)(1),
(2) Date: Apr. 17, 2020

(87) PCT Pub. No.: WO2019/081636
PCT Pub. Date: May 2, 2019

(65) Prior Publication Data
US 2020/0341007 A1 Oct. 29, 2020

(30) Foreign Application Priority Data
Oct. 25, 2017 (EP) ..................................... 17198330

(51) Int. Cl.
*C12Q 1/6876* (2018.01)
*C07K 14/435* (2006.01)
*G01N 33/68* (2006.01)
*C12Q 1/6888* (2018.01)

(52) U.S. Cl.
CPC ....... *G01N 33/6893* (2013.01); *C07K 14/435* (2013.01); *C12Q 1/6876* (2013.01); *C12Q 1/6888* (2013.01); *C12Q 2600/118* (2013.01); *G01N 2800/26* (2013.01)

(58) Field of Classification Search
None
See application file for complete search history.

(56) References Cited

U.S. PATENT DOCUMENTS

| | | | |
|---|---|---|---|
| 9,731,024 B2 | 8/2017 | Siekmann et al. | |
| 2005/0059093 A1 | 3/2005 | Bodmer et al. | |
| 2006/0140943 A1 | 6/2006 | Champion et al. | |
| 2015/0233915 A1* | 8/2015 | Schaller | G01N 33/566 514/789 |
| 2017/0240590 A1 | 8/2017 | Haider et al. | |

FOREIGN PATENT DOCUMENTS

| | | |
|---|---|---|
| WO | WO2012/092539 A2 | 7/2012 |
| WO | WO2015/127029 A1 | 8/2015 |
| WO | WO2016/145426 A1 | 9/2016 |
| WO | WO2017/004159 A1 | 1/2017 |

OTHER PUBLICATIONS

Hildebrand et al. Host-Derived Delta-Like Canonical Notch Ligand 1 as a Novel Diagnostic Biomarker for Bacterial Sepsis—Results form a Combinational Secondary Analysis. Jul. 23, 2019. Frontiers in Cellular and Infection Microbiology. vol. 9, Article 267, pp. 1-9. (Year: 2019).*
Pan et al. Notch Signaling Pathway Was Involved in Regulating Programmed Cell Death 1 Expression during Sepsis-Induced Immunosuppression. Mediators of Inflammation. Vol. 2015, Article ID 539841, 9 pages. (Year: 2015).*
International Search Report and the Written Opinion of International Application No. PCT/EP2018/079273 dated Nov. 16, 2018.
Tjitske S.R. Van Engelen et al: "Biomarkers in Sepsis", Critical Care Clinics, vol. 34, No. 1, Oct. 12, 2017 (Oct. 12, 2017) pp. 139-152, XP055434444, US ISSN: 0749-0704, DOI: 10.1016/j.ccc.2017.08.010.
Pierrakos Charalampos et al: "Sepsis biomarkers: a review", Critical Care Biomed Central Ltd., London, GB, vol. 14, No. 1, Feb. 9, 2010 (Feb. 9, 2010), p. R15, XP021070822, ISSN: 1364-8535.
Toshihiro Ito et al: "The Critical Role of Notch Ligand Delta-like 1 in the Pathogenesis of Influenza A Virus (H1N1) Infection", Plos Pathogens, vol. 7, No. 11, Nov. 3, 2011 (Nov. 3, 2011), p. e1002341, XP055434457, DOI: 10.1371/journal.ppat.1002341 abstract.
Shang Yingli et al: "Role of Notch signaling in regulating innate immunity and inflammation in health and disease", Protein & Cell, Springer Asia, Beijing, CN, vol. 7, No. 3, Mar. 2, 2016 (Mar. 2, 2016), pp. 159-174, XP035966476, ISSN: 1kk674-SOOX, DOI: 10.1007/S13238-016-0250-0 [retrieved on Mar. 2, 2016] abstract.
American Journal of Pathology, vol. 154, No. 3, Mar. 1999, 785-794.
Office Action Chinese Patent Application No. 201880069456.X dated Sep. 16, 2020 with English Summary of Office Action.
Ping SHEN et al., "The value of measurement of serum soluable DLL1 for diagnosis of tuberculous meningitis", Chin J Mod Drug Appl, Jun. 2011, vol. 5, No. 12.
Office Action Japan Patent Application No. 2020-536865 dated Oct. 27, 2020 with English translation of Japanese Office Action.
T Peng et al., Detection of Delta-like 1 ligand for the diagnosis of tuberculous meningitis: An effective and rapid diagnostic method, Journal of International Medical Research, Mar. 20, 2014, vol. 42, No. 3, pp. 728-736.

* cited by examiner

*Primary Examiner* — Channing S Mahatan
(74) *Attorney, Agent, or Firm* — M.J. Ram and Associates

(57) ABSTRACT

The invention refers to a method for in vitro diagnosis of a severe infection comprising determining delta-like ligand 1 protein or a nucleotide sequence coding for delta-like ligand 1 protein in a biological sample wherein an elevated level of expression of delta-like ligand 1 protein or a nucleotide sequence coding for delta-like ligand 1 protein is indicative of a severe infection; and the use of delta-like ligand 1 protein as a biomarker for in vitro diagnosis of a severe infection such as sepsis.

16 Claims, 6 Drawing Sheets
Specification includes a Sequence Listing.

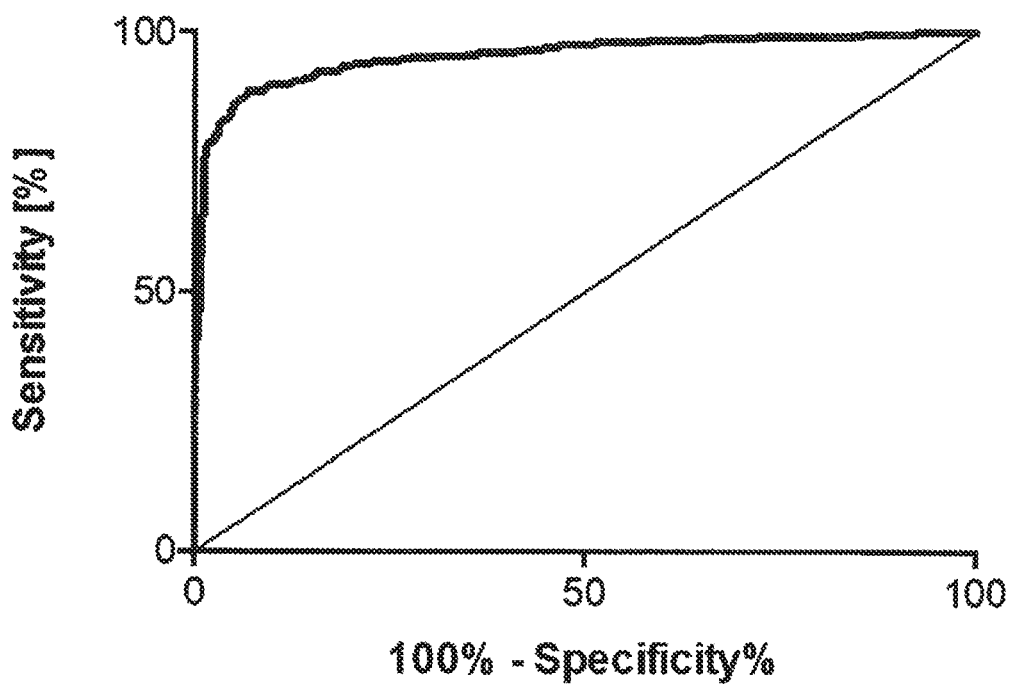
FIGURE 7
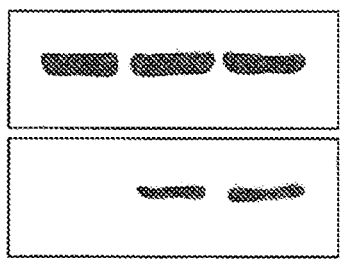
FIGURE 8A
FIGURE 8B

SEQUENCE LISTING

<160> NUMBER OF SEQ ID NOS: 7

<210> SEQ ID NO 1
<211> LENGTH: 15404
<212> TYPE: DNA
<213> ORGANISM: Homo sapiens

<400> SEQUENCE: 1

```
ggggctgatt ccttcgcccc cggctgctgt tcttgtgccc ccaccgtcgc ccaccttcgc      60
gcagagctgc ccgcgccggg ggtcgcgctc ctgcccgctg tggaagcgcg gctgcctggg     120
ggccgcgcgc cttgtgtgca cgcgggcggc gctcacctcc ttcctgcctg cgccagcgct     180
ggtggagcct cgaggtccaa acataaacca gatcgatgcc ccctcccttt tccaggctgt     240
gacgaacgat ggcttcgtgg gcttgtaagt ccacgcgcgg caaccgagtg tgaacacatc     300
tgtgcaccca cttgggtggg cgtggctggg caggggacat ggcccagtga gtgtgtgtgt     360 tgggggtaa ggtctatgtt cacgtgtcca aagacagctt taagaagtaa gcagcaagga     420
agtaaccatg atagctccag gacacagagg cttcgccacg gacgcctctg agaacttccc     480
gtgtggcagc cagcaggtcc attcctctgc tacgttaact gctttcagat tccaaaactg     540
```

```
acggaaggag aatgggcaga gggtggttgg tgcagatgtg ataccaatac taattaataa    600
gcatggtcta cgtcccctte ttcttcttct ttatttcaag taagctggca tgtttgatca    660
acaccagatt tgctgcctgg aagttttta tcttgttatt ctgaacaagg accctaattc     720
ttcttacgaa taagagaacc tctctgttgg gtatacagta ttcagttggt ctgagaaaac    780
acaaacccca ctcaagtctc cagacttgtt tacacagaaa actgaacctg tggctggcct    840
agagtctgag cctattctgg gcattgttta ttgcaatctg cccaggccct cctgccccca    900
ccacagtcac caccacacac gaacctggag aatagaacct ttctttggaa aggggggttg    960
gaataggatt gagtgaccat ggtattaggt catgcacaca ctgctgagga tggccgcact   1020
ggaatttgat aagatgatgg ccataagctt ttattcccag gtggcctcat aaaatggtgg   1080
ggagatactc agtgtctcca gcaaacagag aactccacat gtggttgctg tggctgcagc   1140
tctgatcatt atacagcctg agcttaccct agacactggg gttactcagc ctgtggggtt   1200
gtgctgccca gaaaacaaaa caaaacaaaa aacaccacca ccaggcagca aattcctcct   1260
tccacttctg tgtctgatgt attgggtgcc ttctaagccc taatgagcct cactttgtac   1320
agtaaatttc ctgagacata aaaaagtatt taaaagaaag tttcctgttt tttcctaatg   1380
agcaaggtga ggatttatag tgtggggagg agggactccg gcagccgggg ccaacactga   1440
ggcaagccta tttaacatac cctggcttaa gctccctcct gcgtttgtgg ggttcagagt   1500
gcttagttgt gggagtatag agacatgcag ttagggagtg aaaaaacgcc atttggttcg   1560
gagcagatgg ctggctaggg ggctgatggc gtctaaaggc gtgtcgtccc ctccagctcg   1620
aatccctaag ggctccccctt gtcttcccaa tcaatgaaaa ttaaagtgca agaaaggat   1680
gaatagttgg acctcgagtc tctcctttgt tcatcccagc tactggtgcg caggagttaa   1740
actacaacag gctcctatag aaacgctgaa gttaaacagt ctccccgtta gcacagcttt   1800
ttaaagagag agggagagag gaaccaactt gggggtgggg ggagagaaat ggggagagg   1860
aagaaggaga agaaggagga gaaggaagaa gaggaaggag gtggagtagg agaaagagga   1920
ggaggaggag gaaaagaaaa aggagaacag gaggaggagg aaggagaggg agaagaagaa   1980
aagggctttc tgcttgattt ccccaataca gaatcgcgtg gcataaatta agttggaaaa   2040
gaatgaacgc tttgggcagg attctgatgg attttacgat gcctttcagt tccgctttgc   2100
cgccgtaatc gagaaatctg tgccatgtca atttaacaaa tacttgatac tgaggggggt   2160
ttgttagaga tttggggcaa gtcttttttcc ccccaaggtt taagcccttg cgcgtggaac   2220
ttttttatttc cagttttcta aacaggcatt caaatgagcc tgttttccac ttccattttc   2280
taattaaaag gttcctgata tttcatttct tactgaaatc tacactcagt gttgcaggca   2340
gaggattctg gattctgacc tcgcattctc ttctttttt acatttcttc tgctcctgaa   2400
accctttcac ctaccctcac ccccaccccc agccccagc acagggaaca gctcctgtgc   2460
cttagggaag cagaatgctc cgaagtcagc ttttggagga aacatcaacc tagagaaaaa   2520
aggatcctga cactaggtgg caagattaaa ttaggatttg agctggcccc tccctgtggc   2580
gacagcaagt ccctatagag tccaaaaagg acaccatcat gggggtggca gcatcttctg   2640
aagcctccat ttgctctgaa ccaaacagta gggggtcac ggtgatccca gcctgccttt    2700
ctcacctggc actaaacatc atatgcttgt tcttgtggt taactcttcg ctattccatg    2760
aggcaacagt ggaaaaccta agtggacat ctctgttgat cctaaaactt tacaggtatt    2820
tgggaaacaa ggtagcagga cacaggctgg gtcacttgaa gaggagccgc agagtagcaa   2880
```

-continued

```
ttccagctgc gtagcagccg gagggcctgc cctggacgac ttcaccacgt gaccttcaga    2940
tttctggctg cagtggttgt ccttggtgtt tgaagacttt ccctctgctt agacactttg    3000
atcaagacat tgccgggat gaaagtctcg ttctaccttg acggtgccct gttctcacca     3060
ataaggcagc tctaacacac ctacagtgag gacactgtgg ccaggctgct tccttggggc    3120
tgagctacaa tcaaggggg cactccaaca ctcacctgga accctaatga agctacggag     3180
gtgttggggg tgggcaggga tccacgggcg ggatggtaaa gagagggaga agtgcaaagc    3240
taggtgccag agtaggagtc tctgccccaa cttacttctc catcgtgcct aggagggcaa    3300
tttagataat tcattgtgtc atacgtgtgt tctcggccct cccaataaac tcatttccct    3360
ttaaaaaatg aaaacaaaag ttctagtgtc tgatggacgt gtaaaaccct aataaggtga    3420
cggttgtgta aaggttgtgg gttggggcc ggggctggag gggctttaga acatgcgccg     3480
gacattgttg cagaggccgc ggcgcgcgcg gaggggagct ctttctctcc gcattgtgcg    3540
gggagcaggt gctgtctgca ttaccataca gctgagcgca caaagagcca ctgattcagc    3600
ctcgcacaat aacaggctgc cttaatgaca gccacgcgaa cgacacacac caaactcact    3660
tcttaccagg cggagggagg ccgagggga tacccgggag agaggggccg agacccgggg     3720
aaggtggcgg cggccgagga tcctgtgggg gaggcgcgt gtctgtgggg ggagttgaag     3780
gccaggttct cctggctccg ggatatgct gtccggcccc cgggccccta ctcccagtgg     3840
ccgcggacca cgagaggaca ccgaaggcgc ggggatgcgg gtgtcccagg gggcgtcccg    3900
gccccgcccg cgcgtcggct ctgcactccc cgaggctcag tcgccgtcct gggccaggag    3960
gtgtccccgc ctcggacctc cccaaacttc ccgaaactgc cgcttcgctc tggcagccct    4020
cggcccaccg ctccgcccgc ccctttccta cgatgctccc cgaatcgcca ccccgcctc    4080 cgcccccaag agactcctcc ttaggaagcg cctgccccga agaagggcg gccccgccaa     4140 gagctcgggc ctcgaacttc gtcctcctgc tcgcagccgc cctccccaag ccccgggac    4200 gctgtcggc caaggagacc cctcggctgc cgccgcggcc cggagtttcg gaggccgcgt    4260
cccgccgctc aagtggggcc cgcagcgccg ccccccgcgt gtggccgagg gtctctgggc    4320
gtctgtggcc cggagggcg tgcggagggg acggggcggc ggcaccagct ccagaagcag    4380
ggggattctt gcggtgaaca ttttgcagga atgtaaatga gtgcgttttg tgtggtgagg    4440
gaggaagggg gggctggggg cggggcaggg gaggactgg ggggcgggg aagggtgggg     4500 gcggggagga gggttgcaca ttttacagct cactgaccat ttggcgatcc attgagagga    4560
gggtttggaa aagtggctcc tttgtgacag ctctcgccag attgggggc tgctgatttg     4620 catctcatta gccatgcggg cggccggctg aatataaggg cggcaggcgc ggcgagagc    4680 cagatcctct gcgcgcaccc gcggagaccc gacccggccg agggcagagc gcagggaac    4740 ccgggcagcc gcggcgcaga gcctcctccc acggcccggc cctccggtc ctgcgcgtgt    4800 gtactggatg gcattggctg gattcatcgg aaagacgcgg atctttgctg tgacaccgga   4860
gatcggagcc cggagtgctc ccggaacgac cgccgccgcc gagtgacacc gggccgcgat   4920
ccgcaggggc cgccgcgcac acccgccgcc gccgaccgtc ccctcagcgc gcgccgctgg    4980
ccccggatta tcgccttgcc cgtgggattt ccagaccgcg gctttctaat cggctcggga   5040
ggaagctctg cagctctctt gggaattaag ctcaatctct ggactctctc tctttctctt   5100 tctcccctc cctctcctgc gaagaagctc aagacaaaac caggaagccg gcgaccctca     5160
cctcctcggg ggctgggagg aaggaggaaa acgaaagtcg ccgccgccgc gctgtccccc    5220
gagagctgcc tttcctcggg catccctggg gctgccgcgg gacctcgcag gcggatata     5280
```

-continued

```
aagaaccgcg gccttgggaa gaggcggaga ccggctttta aagaaagaag tcctgggtcc   5340
tgcggtctgg ggcgaggcaa gggcgctttt ctgcccacgc tccccgtggc ccatcgatcc   5400
cccgcgcgtc cgccgctgtt ctaaggagag aagtgggggc ccccaggct  cgcgcgtgga   5460 gcgaagcagc atgggcagtc ggtgcgcgct ggccctggcg gtgctctcgg ccttgctgtg   5520
tcaggtaggc gggcaggtgg gggcgccgcg gccccgcggg gtctcacggg tagccggggc   5580
gcggggcagg agcgcgcggg gaggggcgga cagcggcacg ggccgcgcca gccacggccc   5640
ggaagatgaa tcccgggggc gacgacccca cgcgccggccg tgcagcgagc gcgctcggcc   5700
cctgagccct tccaggctct ccgcacaccc cccacccagg cctcacgccc ctagctcgg    5760 gcgggacccg cgtcctcacg ccccgccct  ccccgtgca ggtctggagc tctggggtgt   5820
tcgaactgaa gctgcaggag ttcgtcaaca agaaggggct gctggggaac cgcaactgct   5880
gccgcggggg cgcggggcca ccgccgtgcg cctgccggac cttcttccgc gtgtgcctca   5940
agcactacca ggccagcgtg tcccccgagc cgccctgcac ctacggcagc gccgtcaccc   6000
ccgtgctggg cgtcgactcc ttcagtctgc ccgacggcgg gggcgccgac tccgcgttca   6060
gcaaccccat ccgcttcccc ttcggcttca cctggccggt gagtgccgca cctgcgcgcg   6120
ccgggccggc cctgaagctg gcggggctgc aggacgcgct gggatcccgc cttgggcgct   6180
cggtggcgga acctcgggga ccccgcgagg cgcaggtggg cgctgcgatc tgcctagcgg   6240
cggccccagg actccagccc agcagcgcgg acacctcgcc ccggggcccc gcggcctgca   6300
ggaggggacc gcgctggggc gaggaggaga ggccgagcgc gcccgggaga tttccgtatc   6360
cggcctctgt gccaggtctc cagtcagagg cgccccttca cgtgggaagg ttctggtttc   6420
ccgactccta gacgcgttgg tggcgcgatt accgcgcag  cgcgaccgct accaccggga   6480
gcgtgcccat cccccaagaa aaatgacaag ggccctcggg cctcttccac cccatcctgc   6540
ctgcattctc tctctctctc taattaaaaa aacaacgtaa tatcctgtag tacaggctga   6600
aaaaacacgt caggaaacca ctcttaaaa  agttcttcca tttccttagg gaaggtgaga   6660
gcaggcagga ggtgcgtgga gaccctctcc agacacgctg ccccagacct gcagccttca   6720
ggcctctgtt gctgacctgg ctgttaggaa tgactgcttt ttgccgtttt cttttcgtta   6780
cctttctggg ttgtctaacg tcttctcccc tctctcccag ggcaccttct ctctgattat   6840
tgaagctctc cacacagatt ctcctgatga cctcgcaaca ggtaaaaaca aaacccaaac   6900
cccaaaactg ctttccccag ttaatagcat tggactttgc ccacccatcc cccagccaaa   6960 cccgacagc  tttcattctg cacgtgcccc agaaagttca gggtggagca gcttgggcct   7020
ccttcccgtg ctgaatgtct cggcccaccc ccgctctgtc ccgagtcaca gggttctcgt   7080
tcagaaccaa ccaggagcat cttctccccg tagaaaaccc agaaagactc atcagccgcc   7140
tggccaccca gaggcacctg acggtgggcg aggagtggtc ccaggacctg cacagcagcg   7200
gccgcacgga cctcaagtac tcctaccgct tcgtgtgtga cgaacactac tacgagagg   7260 gctgctccgt tttctgccgt ccccgggacg atgccttcgg ccacttcacc tgtggggagc   7320
gtggggagaa agtgtgcaac cctggctgga agggcccta  ctgcacagag cgtgagtctc   7380
tgggaaggca ccgctggctc actcgtccac gaacacggac cgcgcgcagg acggggcttc   7440
cctgagccac ggggggcttg ggactgtaga gatgttctgg tggggaaact gaggcccaga   7500
ggacagaagt ggattgctat aagtcacagc tcgtcagtgg gggggttggg gtcaacgcag   7560
acattttaac atcccaggct gtgtttatcc actatcggaa ctgccttcct taatcaggga   7620
```

```
ggattttaga gacagggcca ggggtcagga agtaaagcca gtgctacccc cagggtgtgt    7680
gtattagaga gggagaggag gaaggaaggg aggaacacag agagagcttg tgtgtcaggg    7740
gcaccatttc aacccgagtt cccagtgctg gaacagcatc acactgggaa acgttccatt    7800
ttctctctgg agctggtgtg cttgacctct ctggagcaaa cgcctttccg gatactccct    7860
gtgacacgca ctgtctatgc tggccagaga gcaggctttc actcctgtgg gctgctgagg    7920
ccaggtctcc aaggcctgtg tgggcgaggg gtgcacagcc ccgtctggct tgaatgctca    7980
ggcagcacct tgtctggaga agcaatgtct tcccaatagt gacagaggct ctacctgcct    8040
cttattaggt attgatgtgt caatgtcatg gcaggcaggt gactagggca gggttggggc    8100
cgtgctggct cctggttctg gctcatgggg acctcaggag ccctctctcc agctgactga    8160
ggcctcgcct gcacgcctgg ccgtcccagc ccattggtac cggatttctc tacagctggg    8220
gattgggtag gtcctggagc tgcccagaaa ctccaggaa ctgtcattct ccttccttgg    8280
aactggacaa ccttggagag gggctctggg aggcccagaa cctctggcag gagctgggta    8340
gtgcctgggg ttgagggtgg gtcttcccat tcactgagtg ccttgatgtc cttgctcctt    8400
agcttcccaa attccctccg gaacttactg agctccttct aagctttgcc ttggcctgaa    8460
ctggttctgg ggaaaaacaa aaaaacaaaa aacaacttgt ggagctgctt gttaatgagt    8520
ttcataacca ggcagcaaga gccagctcca agcctcaagc ccactgtcta ctccctgccc    8580
tgcgggagcc tctggccagt ctgctgcctc ccacccttcc tccctgcctc tcttcaccac    8640
agggtagcca gaaacttaaa cttttttctt caaacactga agtctctccc cgcccccagc    8700
tcgcgcgtgc catagattag atctctccgg ggataggcgc agggacaccc gccggctccc    8760
attggcggaa ggggtgcgtg tgcgtgtgtg tgtgtgtgtg tgtgtgtaca cgcgaggggt    8820
gtgtgtgagg aggtgggggcc ggggcgcggg ggaggccgg cattgttgcg ctggggcagc    8880
tgccgtggag gacagacaat ggagcagctg tcctgccctg gcaccctgca taccagctgt    8940
ccactcttat ctgcacacac actttctggg atattaagag gtggagcttt gtgcacagaa    9000
ttgggaagtg ggggaggagg aggggaaga cttctgaccc tctcttagaa gaaaagggga    9060
tagggtgggg gtggggcctt ccgagagccc ttttgtcctt gagcccctgt gttaagaaga    9120
atgctcatcc ccagggctga gtcaagtccc aggctactag gcagggggt cagtcctcca    9180 caacctggga agattaactc agctgggatt tgctgactga agccggcgag ttgtgtcctg    9240
gccccaaggg cggcagccct gttgggacgt acttggcgtg gggcttgacc ctgttttttcc    9300 tttgcttgta gcgatctgcc tgcctggatg tgatgagcag catggatttt gtgacaaacc    9360
aggggaatgc aagtaagtct gcacaaggtg gtgttttgtt ttgttgcctt tcttgttat    9420 cttttcacag ctggtgtatt tgtaaaaaca gccctaggtg atcattcgaa aaactccagt    9480
aagattgatt gaacagggg ccgttttctc atgtttctac ttaatcaatg tttggcagca    9540
tgtaaggtca tggagttgtc attcgtctaa gcccccttaac ggctatgaga atttacagat    9600
agtagtttaa aaagagttgg cacaggaaat gatagtatag ttcaatggtt ctcaaatgtt    9660
gcctcatcct agaatcactc agggagtgat ttttgagatg ctgacactgg tgctgccta    9720 acacccaaga agccagaacc tctggtgggg cccaggccca ggctgcagct cccaaggtga    9780
cccagtgttc tgctaatctg gagaaccaga ggctcactgg tgctgcggga agatggtttc    9840
tagggtgaga atgtccactg caaagccagc aacagtcaac gtccatctga gtcttctgct    9900
tttctccaag gtgcagagtg ggctggcagg gccggtactg tgacgagtgt atccgctatc    9960
caggctgtct ccatggcacc tgccagcagc cctggcagtg caactgccag gaaggctggg   10020
```

```
ggggccttttt ctgcaaccag ggtaagcctt ctctccctga ggcagcctgc tccctccaga   10080
gcagccctgg acttccctgg ctgtttgatc actggaaaaa taaagtcttc ctgcatttga   10140
tgtcgagctt cctatctcct acttttcctg tccccaccct tcacagacct gaactactgc   10200
acacaccata agccctgcaa gaatggagcc acctgcacca acacgggcca ggggagctac   10260
acttgctctt gccggcctgg gtacacaggt gccacctgcg agctggggat tgacgagtgt   10320
gaccccagcc cttgtaagaa cggagggagc tgcacggtga gtcggaggct ccatggcatc   10380
tcacccggaa gctggggtgc cctggtgttg aatggagtgt gtgggctcct tggagcaact   10440
ttggaaagcc ttttctgacc tctccatcgt gtaggatctc gagaacagct actcctgtac   10500
ctgcccaccc ggcttctacg gcaaaatctg tgaattgagt gccatgacct gtgcggacgg   10560
cccttgcttt aacggggtc ggtgctcaga cagcccgat ggagggtaca gctgccgctg   10620
ccccgtgggc tactccggct tcaactgtga gaagaaaatt gactactgca gctcttcacc   10680
ctgttctaat ggtaaggggg cagctggtga ttgctcagag actcgggcga gcggtcaata   10740
ctgaggtggc attaaaaaca agcatttgtg agtgacctcg agtttatgaa tcacttttat   10800
ccagaccgcc aggaattctc gatggaaact ctatctttga gtctggaaag gcctggggaa   10860
tgagagaggc cagggcattt gttatgaagt tctctgtgga aacctagacc aagcagtgaa   10920
tgacttgctc agggccacaa ggtgcttcgg gcacctgcgg ccgcctgagg ttcagtaagt   10980
gatgcccaca ggtgccggcc actccagctt gggaggatgg cccagctgtg tggccaccca   11040
gcacagtagt tggggtgtc cctgagtgag gacagagagc ctcctgctag cagcgagggg   11100
ctggctgccc aaaggagaca cacagcaagg agagctgggc cccagatgtg ccggagcatt   11160
ccggaatggt catccttccc ctccctccct cccctgttgt cagtgcctgc tcctctcact   11220
tgctgtgtaa ctgtgggcaa ggacaccctc gttaagcctc agtttcccca tctgaaacct   11280
gggtcgagtg gcacatgctc ttgcccggct gttgtggcga ctaatgcagc caccagagtg   11340
ttctgcacag cgcctgtcca gatgctggcc gtgtggtttc tgacttgtag agctagacct   11400
ggacacctct cgtatttgag gtcctaaacc atgtcacctt gcgctgtgga ctcattcagg   11460
ccacagactg tctttggttt gtctggtttc tacagtgtca gacagataga tgcttcagag   11520
tgacttttg gtgaacaaac ctacgaggag acacgtgatg ttcatgtccc tgtgttccag   11580
gtgccaagtg tgtggacctc ggtgatgcct acctgtgccg ctgccaggcc ggcttctcgg   11640
ggaggcactg tgacgacaac gtggacgact gcgcctcctc cccgtgcgcc aacggggca   11700
cctgccggga tggcgtgaac gacttctcct gcacctgccc gcctggctac acgggcagga   11760
actgcagtgc cccgtcagc aggtgcgagc acgcaccctg ccacaatggg gccacctgcc   11820
acgagaggg ccaccgctat gtgtgcgagt gtgcccgagg ctacggggt cccaactgcc   11880
agttcctgct ccccgagctg ccccgggcc cagcggtggt ggacctcact gagaagctag   11940
agggccaggg cgggccattc ccctgggtgg ccgtgtgcgc cggggtcatc cttgtcctca   12000
tgctgctgct gggctgtgcc gctgtggtgg tctgcgtccg gctgaggctg cagaagcacc   12060
ggccccagc cgacccctgc cggggggaga cggagaccat gaacaacctg gccaactgcc   12120
agcgtgagaa ggacatctca gtcagcatca tcggggccac gcagatcaag aacaccaaca   12180
agaaggcgga cttccacggg gaccacagcg ccgacaagaa tggcttcaag gcccgctacc   12240
cagcggtgga ctataacctc gtgcaggacc tcaaggtga cgacaccgcc gtcagggacg   12300
cgcacagcaa gcgtgacacc aagtgccagc cccagggctc ctcaggggag gagaagggga   12360
```

```
ccccgaccac actcagggggg tgcgtgctgc gggccgggca tcaggagggg gtacctggggg    12420 ggtgtcttcc tggaaccact gctccgtttc tcttcccaaa tgttctcatg cattcattgt    12480
ggattttctc tattttcctt ttagtggaga agcatctgaa agaaaaaggc cggactcggg    12540
ctgttcaact tcaaaagaca ccaagtacca gtcggtgtac gtcatatccg aggagaagga    12600
tgagtgcgtc atagcaactg aggtcagtgc aggcagcagc cgctccctcc tcctcggcat    12660
gggagcacct gaagctggag cacgggaatc ggtctcaggc taacttccca tttgtcttgt    12720
ggccccccag gtgtaaaatg aagtgagat ggcaagactc ccgtttctct taaaataagt     12780
aaaattccaa ggatatatgc cccaacgaat gctgctgaag aggagggagg cctcgtggac    12840
tgctgctgag aaaccgagtt cagaccgagc aggttctcct cctgaggtcc tcgacgcctg    12900
ccgacagcct gtcgcggccc ggccgcctgc ggcactgcct tccgtgacgt cgccgttgca    12960
ctatggacag ttgctcttaa gagaatatat atttaaatgg gtgaactgaa ttacgcataa    13020
gaagcatgca ctgcctgagt gtatattttg gattcttatg agccagtctt ttcttgaatt    13080
agaaacacaa acactgcctt tattgtcctt tttgatacga agatgtgctt tttctagatg    13140
gaaaagatgt gtgttatttt ttggatttgt aaaaatattt ttcatgatat ctgtaaagct    13200
tgagtatttt gtgatgttcg tttttttataa tttaaatttt ggtaaatatg tacaaaggca    13260
cttcgggtct atgtgactat atttttttgt atataaatgt atttatggaa tattgtgcaa    13320
atgttatttg agtttttac tgtttttgtta atgaagaaat tccttttttaa aatattttc    13380 caaaataaat tttatgaatg acaaccagaa ggcgtagtta cttggctttg ccttagagcg    13440
gaggtgtgct cactcacctg cggcccgcga ggctgagggc agaggtggcc ttggtgtttc    13500
tcttttcaag gctttggttt ccctggatcc atgagaagca gcccgttcct ctcctccctc    13560
aggaagctgc ttgctggcca tcatgaggtg acttggtaag agcaggcacg cgcatgaagc    13620
agccgcgatt ttctaattcc atccccccat gcatttatta gttctttccg cagaaagaat    13680
gagcgttcct cattcattca ttcattcatt cattcattca ttcattcatg tcagtgtaga    13740
cttgtgagtt attttgtacc cagtgggtca cagctgtcat gattttgtcg ccgtttgacg    13800
ccaacatggc cccagacggg gcgtgggagt cacggaagct gctcctccgc ttcccgtcgg    13860
tgggcagccc cgtctctaag cgcgtcccgc ctgctggctc agcaggaccg cacgggctcc    13920
ctgtgggctg acccctcatt tgccgctttg ccccccgcta agcccgggtt ccttatggta    13980
gtgattgcat ttttaacttg cgcgtacctc aaagcgctga gcggttccca ggatggaaag    14040
agggcgaccg atgtagcagg agctgcgcgg aggcactggc gctcactccc ctcagacccg    14100
actccgcttg catttcctcc ttgcattaag ggcacgttaa atgccaggcc agcaacacca    14160
gcaaagagga gaagtgtttt gctaagaaca ttgagcttga atccgatgac agctctcagt    14220
ctcattacca gttacggaaa cacgggactg aaaactcctt cctcgacgcc ccacgcatct    14280
gcgcagccga atccagggaa ctctgtagcc aaataaattg caaggaaaaa acaagaaaat    14340
ggtgaggggg aacccataga tacaaagaga cacggacata tcaatccatc gcagcgtctg    14400
gatctggttc ctgtttcaaa cagtttaaaa attttatgaa cccactggag acatgtaagc    14460
gctgactggg atatccacat gattttaaag tgcacctgct aaatagttta gatgtgatgt    14520
gttattactg ttcagtttaa aaagagacct tatctttag agaaaattct gaaatattta     14580
tggatgaaac aatacgaggc ctgggactga ttcggagccc ccgccgcgg gcacggtggc      14640 acggggagtc ccacgagcac tgctgggggt cgctgcagct gggagtggcc catggggcg      14700 ctcacttccg tgttctttcc tctttcgtac acgtttgaaa cttcccataa gcaaaagcat    14760
```

```
taagccggac catacagtga atacacgcac acgcaaacac gacagtttcc gggtgtgtat    14820
ggaccgccgt gtctgtgacg tgacccacag cagaatgcat ctgagggagg cttgctgtgg    14880
ttgcatacgc acatcgcaga tgagaaatct tacaaggcca aaagcaagcc aattaaactg    14940
ggtggagagc gggagtccgg tcaaggacgc tggtagcaga gtctcaggct cgctggtggc    15000
gcgcctaggt gattgcccac tctgctgagt ccttgaaagg gaaacggcag cgtctgcagc    15060
agtgctggga gcacctcctc ccgtctgcag gggacggtgc ctttcagggc acggttctgc    15120
gcatgtgctc agctggcgcc agcgaacggc ttccggctgc tcttagcgtg gagttcaaaa    15180
tccttgactt ggcctctcag gtcatgcacc atccggctcc cgcctgtctt ggagcctcgt    15240
ttcgttattc tcccacgggt ctgttaccgc tcggctccag ccagcgccct ggcagcctgg    15300
ttctccatcc gccccactc tgcgactttg agtgggatct tccatctgtc tggtgacttc    15360
cagtgtgacc ttcttccgcc acgaaaatga cccgcctggg ttac                    15404

<210> SEQ ID NO 2
<211> LENGTH: 723
<212> TYPE: PRT
<213> ORGANISM: Homo sapiens

<400> SEQUENCE: 2

Met Gly Ser Arg Cys Ala Leu Ala Leu Ala Val Leu Ser Ala Leu Leu
1               5                   10                  15

Cys Gln Val Trp Ser Ser Gly Val Phe Glu Leu Lys Leu Gln Glu Phe
                20                  25                  30

Val Asn Lys Lys Gly Leu Leu Gly Asn Arg Asn Cys Cys Arg Gly Gly
            35                  40                  45

Ala Gly Pro Pro Pro Cys Ala Cys Arg Thr Phe Phe Arg Val Cys Leu
        50                  55                  60

Lys His Tyr Gln Ala Ser Val Ser Pro Glu Pro Cys Thr Tyr Gly
65                  70                  75                  80

Ser Ala Val Thr Pro Val Leu Gly Val Asp Ser Phe Ser Leu Pro Asp
                85                  90                  95

Gly Gly Gly Ala Asp Ser Ala Phe Ser Asn Pro Ile Arg Phe Pro Phe
            100                 105                 110

Gly Phe Thr Trp Pro Gly Thr Phe Ser Leu Ile Ile Glu Ala Leu His
        115                 120                 125

Thr Asp Ser Pro Asp Asp Leu Ala Thr Glu Asn Pro Glu Arg Leu Ile
    130                 135                 140

Ser Arg Leu Ala Thr Gln Arg His Leu Thr Val Gly Glu Glu Trp Ser
145                 150                 155                 160

Gln Asp Leu His Ser Ser Gly Arg Thr Asp Leu Lys Tyr Ser Tyr Arg
                165                 170                 175

Phe Val Cys Asp Glu His Tyr Tyr Gly Glu Gly Cys Ser Val Phe Cys
            180                 185                 190

Arg Pro Arg Asp Asp Ala Phe Gly His Phe Thr Cys Gly Glu Arg Gly
        195                 200                 205

Glu Lys Val Cys Asn Pro Gly Trp Lys Gly Pro Tyr Cys Thr Glu Pro
    210                 215                 220

Ile Cys Leu Pro Gly Cys Asp Glu Gln His Gly Phe Cys Asp Lys Pro
225                 230                 235                 240

Gly Glu Cys Lys Cys Arg Val Gly Trp Gln Gly Arg Tyr Cys Asp Glu
                245                 250                 255
```

-continued

```
Cys Ile Arg Tyr Pro Gly Cys Leu His Gly Thr Cys Gln Gln Pro Trp
            260                 265                 270

Gln Cys Asn Cys Gln Glu Gly Trp Gly Gly Leu Phe Cys Asn Gln Asp
        275                 280                 285

Leu Asn Tyr Cys Thr His His Lys Pro Cys Lys Asn Gly Ala Thr Cys
        290                 295                 300

Thr Asn Thr Gly Gln Gly Ser Tyr Thr Cys Ser Cys Arg Pro Gly Tyr
305                 310                 315                 320

Thr Gly Ala Thr Cys Glu Leu Gly Ile Asp Glu Cys Asp Pro Ser Pro
                325                 330                 335

Cys Lys Asn Gly Gly Ser Cys Thr Asp Leu Glu Asn Ser Tyr Ser Cys
                340                 345                 350

Thr Cys Pro Pro Gly Phe Tyr Gly Lys Ile Cys Glu Leu Ser Ala Met
        355                 360                 365

Thr Cys Ala Asp Gly Pro Cys Phe Asn Gly Gly Arg Cys Ser Asp Ser
        370                 375                 380

Pro Asp Gly Gly Tyr Ser Cys Arg Cys Pro Val Gly Tyr Ser Gly Phe
385                 390                 395                 400

Asn Cys Glu Lys Lys Ile Asp Tyr Cys Ser Ser Ser Pro Cys Ser Asn
                405                 410                 415

Gly Ala Lys Cys Val Asp Leu Gly Asp Ala Tyr Leu Cys Arg Cys Gln
                420                 425                 430

Ala Gly Phe Ser Gly Arg His Cys Asp Asp Asn Val Asp Asp Cys Ala
        435                 440                 445

Ser Ser Pro Cys Ala Asn Gly Gly Thr Cys Arg Asp Gly Val Asn Asp
450                 455                 460

Phe Ser Cys Thr Cys Pro Pro Gly Tyr Thr Gly Arg Asn Cys Ser Ala
465                 470                 475                 480

Pro Val Ser Arg Cys Glu His Ala Pro Cys His Asn Gly Ala Thr Cys
                485                 490                 495

His Glu Arg Gly His Arg Tyr Val Cys Glu Cys Ala Arg Gly Tyr Gly
                500                 505                 510

Gly Pro Asn Cys Gln Phe Leu Leu Pro Glu Leu Pro Pro Gly Pro Ala
        515                 520                 525

Val Val Asp Leu Thr Glu Lys Leu Glu Gly Gln Gly Gly Pro Phe Pro
        530                 535                 540

Trp Val Ala Val Cys Ala Gly Val Ile Leu Val Leu Met Leu Leu Leu
545                 550                 555                 560

Gly Cys Ala Ala Val Val Val Cys Val Arg Leu Arg Leu Gln Lys His
                565                 570                 575

Arg Pro Pro Ala Asp Pro Cys Arg Gly Glu Thr Glu Thr Met Asn Asn
        580                 585                 590

Leu Ala Asn Cys Gln Arg Glu Lys Asp Ile Ser Val Ser Ile Ile Gly
        595                 600                 605

Ala Thr Gln Ile Lys Asn Thr Asn Lys Lys Ala Asp Phe His Gly Asp
        610                 615                 620

His Ser Ala Asp Lys Asn Gly Phe Lys Ala Arg Tyr Pro Ala Val Asp
625                 630                 635                 640

Tyr Asn Leu Val Gln Asp Leu Lys Gly Asp Asp Thr Ala Val Arg Asp
                645                 650                 655

Ala His Ser Lys Arg Asp Thr Lys Cys Gln Pro Gln Gly Ser Ser Gly
        660                 665                 670

Glu Glu Lys Gly Thr Pro Thr Thr Leu Arg Gly Gly Glu Ala Ser Glu
```

```
                    675                 680                 685
Arg Lys Arg Pro Asp Ser Gly Cys Ser Thr Ser Lys Asp Thr Lys Tyr
        690                 695                 700
Gln Ser Val Tyr Val Ile Ser Glu Glu Lys Asp Glu Cys Val Ile Ala
705                 710                 715                 720
Thr Glu Val

<210> SEQ ID NO 3
<211> LENGTH: 247
<212> TYPE: PRT
<213> ORGANISM: Homo sapiens

<400> SEQUENCE: 3

Met Gly Ser Arg Cys Ala Leu Ala Leu Ala Val Leu Ser Ala Leu Leu
1               5                   10                  15
Cys Gln Val Trp Ser Ser Gly Val Phe Glu Leu Lys Leu Gln Glu Phe
            20                  25                  30
Val Asn Lys Lys Gly Leu Leu Gly Asn Arg Asn Cys Cys Arg Gly Gly
        35                  40                  45
Ala Gly Pro Pro Cys Ala Cys Arg Thr Phe Phe Arg Val Cys Leu
    50                  55                  60
Lys His Tyr Gln Ala Ser Val Ser Pro Glu Pro Pro Cys Thr Tyr Gly
65                  70                  75                  80
Ser Ala Val Thr Pro Val Leu Gly Val Asp Ser Phe Ser Leu Pro Asp
                85                  90                  95
Gly Gly Gly Ala Asp Ser Ala Phe Ser Asn Pro Ile Arg Phe Pro Phe
            100                 105                 110
Gly Phe Thr Trp Pro Gly Thr Phe Ser Leu Ile Ile Glu Ala Leu His
        115                 120                 125
Thr Asp Ser Pro Asp Asp Leu Ala Thr Glu Asn Pro Glu Arg Leu Ile
    130                 135                 140
Ser Arg Leu Ala Thr Gln Arg His Leu Thr Val Gly Glu Glu Trp Ser
145                 150                 155                 160
Gln Asp Leu His Ser Ser Gly Arg Thr Asp Leu Lys Tyr Ser Tyr Arg
                165                 170                 175
Phe Val Cys Asp Glu His Tyr Tyr Gly Glu Gly Cys Ser Val Phe Cys
            180                 185                 190
Arg Pro Arg Asp Asp Ala Phe Gly His Phe Thr Cys Gly Glu Arg Gly
        195                 200                 205
Glu Lys Val Cys Asn Pro Gly Trp Lys Gly Pro Tyr Cys Thr Glu Arg
    210                 215                 220
Glu Ser Leu Gly Arg His Arg Trp Leu Thr Arg Pro Arg Thr Arg Thr
225                 230                 235                 240
Thr Arg Arg Asp Gly Ala Ser
                245

<210> SEQ ID NO 4
<211> LENGTH: 522
<212> TYPE: PRT
<213> ORGANISM: Homo sapiens

<400> SEQUENCE: 4

Ser Gly Val Phe Glu Leu Lys Leu Gln Glu Phe Val Asn Lys Lys Gly
1               5                   10                  15
Leu Leu Gly Asn Arg Asn Cys Cys Arg Gly Gly Ala Gly Pro Pro Pro
            20                  25                  30
```

```
Cys Ala Cys Arg Thr Phe Phe Arg Val Cys Leu Lys His Tyr Gln Ala
        35                  40                  45
Ser Val Ser Pro Glu Pro Cys Thr Tyr Gly Ser Ala Val Thr Pro
    50                  55                  60
Val Leu Gly Val Asp Ser Phe Ser Leu Pro Asp Gly Gly Ala Asp
65                  70                  75                  80
Ser Ala Phe Ser Asn Pro Ile Arg Phe Pro Phe Gly Phe Thr Trp Pro
                85                  90                  95
Gly Thr Phe Ser Leu Ile Ile Glu Ala Leu His Thr Asp Ser Pro Asp
                100                 105                 110
Asp Leu Ala Thr Glu Asn Pro Glu Arg Leu Ile Ser Arg Leu Ala Thr
                115                 120                 125
Gln Arg His Leu Thr Val Gly Glu Glu Trp Ser Gln Asp Leu His Ser
        130                 135                 140
Ser Gly Arg Thr Asp Leu Lys Tyr Ser Tyr Arg Phe Val Cys Asp Glu
145                 150                 155                 160
His Tyr Tyr Gly Glu Gly Cys Ser Val Phe Cys Arg Pro Arg Asp Asp
                165                 170                 175
Ala Phe Gly His Phe Thr Cys Gly Glu Arg Gly Glu Lys Val Cys Asn
                180                 185                 190
Pro Gly Trp Lys Gly Pro Tyr Cys Thr Glu Pro Ile Cys Leu Pro Gly
            195                 200                 205
Cys Asp Glu Gln His Gly Phe Cys Asp Lys Pro Gly Glu Cys Lys Cys
    210                 215                 220
Arg Val Gly Trp Gln Gly Arg Tyr Cys Asp Glu Cys Ile Arg Tyr Pro
225                 230                 235                 240
Gly Cys Leu His Gly Thr Cys Gln Gln Pro Trp Gln Cys Asn Cys Gln
            245                 250                 255
Glu Gly Trp Gly Gly Leu Phe Cys Asn Gln Asp Leu Asn Tyr Cys Thr
        260                 265                 270
His His Lys Pro Cys Lys Asn Gly Ala Thr Cys Thr Asn Thr Gly Gln
        275                 280                 285
Gly Ser Tyr Thr Cys Ser Cys Arg Pro Gly Tyr Thr Gly Ala Thr Cys
    290                 295                 300
Glu Leu Gly Ile Asp Glu Cys Asp Pro Ser Pro Cys Lys Asn Gly Gly
305                 310                 315                 320
Ser Cys Thr Asp Leu Glu Asn Ser Tyr Ser Cys Thr Cys Pro Pro Gly
                325                 330                 335
Phe Tyr Gly Lys Ile Cys Glu Leu Ser Ala Met Thr Cys Ala Asp Gly
            340                 345                 350
Pro Cys Phe Asn Gly Gly Arg Cys Ser Asp Ser Pro Asp Gly Gly Tyr
        355                 360                 365
Ser Cys Arg Cys Pro Val Gly Tyr Ser Gly Phe Asn Cys Glu Lys Lys
    370                 375                 380
Ile Asp Tyr Cys Ser Ser Ser Pro Cys Ser Asn Gly Ala Lys Cys Val
385                 390                 395                 400
Asp Leu Gly Asp Ala Tyr Leu Cys Arg Cys Gln Ala Gly Phe Ser Gly
                405                 410                 415
Arg His Cys Asp Asp Asn Val Asp Asp Cys Ala Ser Ser Pro Cys Ala
            420                 425                 430
Asn Gly Gly Thr Cys Arg Asp Gly Val Asn Asp Phe Ser Cys Thr Cys
        435                 440                 445
```

```
Pro Pro Gly Tyr Thr Gly Arg Asn Cys Ser Ala Pro Val Ser Arg Cys
    450                 455                 460

Glu His Ala Pro Cys His Asn Gly Ala Thr Cys His Glu Arg Gly His
465                 470                 475                 480

Arg Tyr Val Cys Glu Cys Ala Arg Gly Tyr Gly Gly Pro Asn Cys Gln
                485                 490                 495

Phe Leu Leu Pro Glu Leu Pro Pro Gly Pro Ala Val Val Asp Leu Thr
            500                 505                 510

Glu Lys Leu Glu Gly Gln Gly Gly Pro Phe
        515                 520

<210> SEQ ID NO 5
<211> LENGTH: 180
<212> TYPE: PRT
<213> ORGANISM: Homo sapiens

<400> SEQUENCE: 5

Pro Trp Val Ala Val Cys Ala Gly Val Ile Leu Val Leu Met Leu Leu
1               5                   10                  15

Leu Gly Cys Ala Ala Val Val Cys Val Arg Leu Arg Leu Gln Lys
            20                  25                  30

His Arg Pro Pro Ala Asp Pro Cys Arg Gly Glu Thr Glu Thr Met Asn
        35                  40                  45

Asn Leu Ala Asn Cys Gln Arg Glu Lys Asp Ile Ser Val Ser Ile Ile
    50                  55                  60

Gly Ala Thr Gln Ile Lys Asn Thr Asn Lys Lys Ala Asp Phe His Gly
65                  70                  75                  80

Asp His Ser Ala Asp Lys Asn Gly Phe Lys Ala Arg Tyr Pro Ala Val
                85                  90                  95

Asp Tyr Asn Leu Val Gln Asp Leu Lys Gly Asp Asp Thr Ala Val Arg
            100                 105                 110

Asp Ala His Ser Lys Arg Asp Thr Lys Cys Gln Pro Gln Gly Ser Ser
        115                 120                 125

Gly Glu Glu Lys Gly Thr Pro Thr Thr Leu Arg Gly Gly Glu Ala Ser
    130                 135                 140

Glu Arg Lys Arg Pro Asp Ser Gly Cys Ser Thr Ser Lys Asp Thr Lys
145                 150                 155                 160

Tyr Gln Ser Val Tyr Val Ile Ser Glu Glu Lys Asp Glu Cys Val Ile
                165                 170                 175

Ala Thr Glu Val
            180

<210> SEQ ID NO 6
<211> LENGTH: 154
<212> TYPE: PRT
<213> ORGANISM: Homo sapiens

<400> SEQUENCE: 6

Arg Leu Arg Leu Gln Lys His Arg Pro Pro Ala Asp Pro Cys Arg Gly
1               5                   10                  15

Glu Thr Glu Thr Met Asn Asn Leu Ala Asn Cys Gln Arg Glu Lys Asp
            20                  25                  30

Ile Ser Val Ser Ile Ile Gly Ala Thr Gln Ile Lys Asn Thr Asn Lys
        35                  40                  45

Lys Ala Asp Phe His Gly Asp His Ser Ala Asp Lys Asn Gly Phe Lys
    50                  55                  60
```

```
Ala Arg Tyr Pro Ala Val Asp Tyr Asn Leu Val Gln Asp Leu Lys Gly
 65              70                  75                  80

Asp Asp Thr Ala Val Arg Asp Ala His Ser Lys Arg Asp Thr Lys Cys
             85                  90                  95

Gln Pro Gln Gly Ser Ser Gly Glu Glu Lys Gly Thr Pro Thr Thr Leu
            100                 105                 110

Arg Gly Gly Glu Ala Ser Glu Arg Lys Arg Pro Asp Ser Gly Cys Ser
        115                 120                 125

Thr Ser Lys Asp Thr Lys Tyr Gln Ser Val Tyr Val Ile Ser Glu Glu
        130                 135                 140

Lys Asp Glu Cys Val Ile Ala Thr Glu Val
145                 150

<210> SEQ ID NO 7
<211> LENGTH: 26
<212> TYPE: PRT
<213> ORGANISM: Homo sapiens

<400> SEQUENCE: 7

Pro Trp Val Ala Val Cys Ala Gly Val Ile Leu Val Leu Met Leu Leu
 1               5                  10                  15

Leu Gly Cys Ala Ala Val Val Val Cys Val
            20                  25
```

DELTA-LIKE LIGAND 1 FOR DIAGNOSING SEVERE INFECTIONS

This application claims benefit of PCT/EP2018/079273 filed Oct. 25, 2018 which claims priority of EP17198330.7 filed Oct. 25, 2017.

TECHNICAL FIELD OF THE INVENTION

The invention relates to the use of delta-like ligand 1 as a biomarker in the diagnosis of severe infections and to a method for a quick in vitro diagnosing of severe infections such as sepsis by controlling the delta-like ligand 1 level in a biological sample.

BACKGROUND OF THE INVENTION

Biomarkers are measurable characteristics of an organism that reflect a particular physiological state. In medicine, biomarkers are often compounds isolated from biological tissue that can be used as an indicator of the presence or severity of a particular disease state or monitor the effectiveness of a given intervention.

Biomarkers are particularly useful in the diagnosis and possibly prognosis of a disease, as well as in monitoring disease progression or response to treatment. The ideal biomarker should be easily obtained and measured and should be reliable in that it shows both a high sensitivity and specificity for a disease.

Severe infections, and in particular sepsis, are particularly evasive medical conditions for which no highly reliable biomarkers are present. Severe infection including sepsis, are identified by and/or may result in life-threatening organ failure evoked by a dysregulated immune response to infection. In sepsis, the host response that is triggered by microbial pathogens peaks in a pathological syndrome that is characterized by exaggerated inflammation and a subsequent immune suppression.

Despite the steady improvements in critical care medicine and anti-microbial therapies, such infection remains a leading cause of death in intensive care units across all age groups worldwide. In order to improve outcomes and simultaneously avoid unnecessary antibiotic treatment, a rapid and reliable test for diagnosing a severe infection is essential.

Sepsis is a severe and thus life-threatening infection. Up to now, blood cultures remain the gold standard in diagnosing sepsis, however blood cultures take time and many patients who have signs and symptoms of sepsis have negative blood cultures. Therefore, a supplementary approach for diagnosing a severe infection, and in particular for diagnosing sepsis is urgently needed.

C. Pierrakos and J. L. Vincent (2010) *Critical Care*, 14:R15 describe biomarkers known in the art to be useful for identifying or ruling out sepsis. These include various biomarkers directed to cytokines/chemokines, cells, receptors, coagulation, vascular endothelial damage, vasodilation, organ dysfunction, and acute phase proteins. Notch ligands, and in particular delta-like ligand 1, are not mentioned.

Van Engelen et al. (2018) "Biomarkers in Sepsis", *Critical Care Clinics*, 34(1):129-152 describes various biomarkers for diagnosing sepsis and in particular points to the omics (i.e. genomics, epigenetics, transcriptomics, proteomics, and metabolomics) field of systems biology as being a promising tool for the discovery of novel biomarkers.

WO 2016/145,426 A1 describes a method for diagnosing sepsis using expression levels of CEACAM1, ZDHHC19, C9orf95, GNA15, BATF, C3AR1, KIAA1370, TGFBI, MTCH1, RPGRIP1, and HLA-DPB1 as biomarkers.

U.S. 2005/059,093 A1 describes a method for detecting modulators of Notch signaling comprising the step of monitoring Notch signaling in a cell of the immune system in the presence and absence of a candidate modulator and determining whether the candidate modulator modulates Notch signaling.

WO 2017/004,159 A1 describes compositions that bind to and inhibit the biological activity of soluble biomolecules to inhibit the target or pathogen from interacting with other molecules or cells. Notch ligands, including Delta-like ligand 1 (DLL1) are mentioned as being particularly useful for treating or preventing atherosclerosis, calcific aortic valve stenosis, heart failure, stroke, and cancer. To treat or prevent sepsis associated with an infection caused by a pathogen, WO 2017/004,159A1 proposes selectively binding TNFα, interleukin 1, interleukin 6, interleukin 8, interleukin 12, interferon gamma, macrophage migration inhibitory factor, GM-CSF, and/or a blood clotting factor.

U.S. 2006/140,943 A1 describes a use of a modulator of Notch signaling for the preparation of a medicament for treatment of Graft Versus Host Disease (GVHD) and diseases and conditions caused by or associated with transplants such as organ, tissue and/or cell transplants (e.g. bone marrow transplants), wherein the modulator is used to reduce the reactivity of cells of the immune system.

WO 2012/092,539 A2 describes an antibody against DLL4 and a method for treating a DLL4-associated disease, such as a cell proliferative disorder or a pathological condition associated with angiogenesis. WO 2012/092,539 A2 describes that dysregulation of angiogenesis can lead to neoplastic and non-neoplastic disorders, and names sepsis as one of many of such non-neoplastic disorders.

U.S. Pat. No. 9,731,024B2 and U.S. 2017/0240590 A1 describe materials and methods of conjugating a water soluble polymer to an oxidized carbohydrate moiety of a therapeutic protein. One of many proteins listed as therapeutic proteins is delta-like protein 1.

Several biomarkers are currently used to diagnose a severe infection such as sepsis. The acute phase proteins procalcitonin (PCT) and C-reactive protein (CRP), together with leukocyte count, have been most widely used.

Nonetheless, the effectiveness of PCT and CRP are restricted by their lack of specificity and sensitivity for sepsis. In particular, it remains difficult to differentiate sepsis from other non-infectious causes of inflammation. Therefore, new sepsis biomarkers with higher reliability are required.

SUMMARY

The problem underlying the invention is providing a biomarker that can be used to diagnose a severe infection with a high level of reliability.

This problem is solved by the use of delta-like ligand 1 protein (DLL1) or a nucleotide sequence coding for delta-like ligand 1 protein as a biomarker for the in vitro (ex vivo) diagnosis of a severe infection. Accordingly, an elevated level of delta-like ligand 1 protein or a nucleotide sequence coding for delta-like ligand 1 protein in a patient's biological sample is indicative for the presence of a severe infection.

Further, the invention concerns a method for in vitro diagnosis of a severe infection comprising determining delta-like ligand 1 protein or a nucleotide sequence coding for delta-like ligand 1 protein in a biological sample wherein an elevated level of expression of delta-like ligand 1 protein or of a nucleotide sequence coding for delta-like ligand 1 protein is indicative of an infection.

Surprisingly, it was found that delta-like ligand 1 acts as a biomarker for severe infections, in particular sepsis with a high level of reliability. Advantages associated with this diagnostic biomarker of the invention are earlier diagnosis of the infection, timely treatment, and improved disease outcome. It will also reduce unnecessary costs associated with testing other biomarkers that show lower sensitivity and selectivity than delta-like ligand 1.

DETAILED DESCRIPTION

Delta-like proteins are single-pass transmembrane proteins known for their role in Notch signaling as homologs of the Notch Delta ligand first described in *Drosophila*. Synonyms of DLL-1 are delta-like-ligand 1, delta-like protein, H-Delta, 1, drosophila Delta homolog 1, delta like canonical Notch ligand 1, DL1, Notch ligand deltal-like1. In mammals, there are three delta-like genes encoding delta-like ligand 1 (DLL1 encoding DLL1), delta-like ligand 3 (DLL3 encoding DLL3), and delta-like ligand 4 (DLL4 encoding DLL4), all ligands comprising a conserved cysteine-rich region known as the DSL (Delta, Serrate, Lag2) domain, several epidermal growth factor (EGF)-like repeats, and a transmembrane domain. The amino acid sequence of delta-like ligand 1 protein and the nucleotide sequence coding for delta-like ligand 1 protein are known. For example, an amino acid sequence of DLL1 is described in American Journal of Pathology, Vol. 154, No. 3, March 1999, 785-794 or in the database of the National Center for Biotechnology Information (https://www.ncbi.nlm.nih.gov/protein/NP_005609.3). The chromosomal location of the human orthologue is 6q27.

The delta-like ligand 1 protein as used in the invention can be a protein that is encoded by the nucleotide sequence SEQ ID NO: 1 or a nucleotide sequence which is at least 80%, preferably 85% or 90% identical to SEQ ID NO: 1.

Further, the delta-like ligand 1 protein can be a protein having at least 90% identity, particularly 95% identity with amino acid sequence SEQ ID NO: 2 or SEQ ID NO: 3.

The term delta-ligand 1 protein as used herein for the purposes of the invention also includes naturally occurring cleavage products of DLL1. Naturally occurring cleavage products according to the invention comprise extracellular, transmembrane, and intracellular cleavage products. In a preferred embodiment, the naturally occurring cleavage product is an extracellular cleavage product. Thus, the term delta-ligand 1 protein also includes polypeptides consisting essentially of N- or C-terminal fragments of the protein according to SEQ ID NO: 2 and which are elevated at a severe infection, in particular sepsis. Thus, the term DLL1 protein comprises post-translational modifications, natural proteolytic and processed DLL1 protein. It also comprises the soluble, insoluble DLL1 protein and naturally occurring isoforms of DLL1 protein of SEQ ID NOs: 2 or 3 (UniProtKB-000548 (DLL1_HUMAN). Such appropriate natural cleavage products of DLL1 are, for example, represented by amino acid SEQ ID NO: 4, SEQ ID NO: 5, SEQ ID NO: 6 and/or SEQ ID NO: 7. SEQ ID NO: 4 represents the soluble DLL1 protein. SEQ ID NO: 5 represents the transmembrane domain of the DLL1 protein linked to the intracellular domain of the DLL1 protein. SEQ ID NO: 6 represents the intracellular domain of the DLL1 protein. SEQ ID NO: 7 represents the transmembrane domain of the DLL1 protein.

Further comprised within the term DLL1 proteins are proteins which are modified, for example, by phosphorylation, methylation, acetylation and glycosylation.

In the embodiments the level of DLL1 protein and/or the level of a DLL1 nucleotide sequence is/are determined. As used herein, the term nucleotide sequence may refer to DNA, cDNA, RNA, or mRNA. The nucleotide sequence coding for the DLL1 protein or for a protein isoform of DLL1 can also be a splice variant on RNA level. Such splice variants, for example are, nucleotide sequences without the N-terminal or without the C-terminal of the sequence.

According to one embodiment of the invention, when using the DLL1 nucleotide sequence as a biomarker for diagnosing an infection or in a method for in vitro diagnosing an infection, an elevated expression level of DLL1 is indicative of a severe infection. Exemplary nucleotide sequences of DLL1 in the determination of the expression level are SEQ ID NO: 1.

References to the nucleotide sequence DLL1 labeled SEQ ID NO: 1 refer to the DNA sequence in *Homo sapiens*. It will, however, be evident that the invention is not limited to *Homo sapiens*, but rather extends to all mammals.

The term "elevated" as used herein means an increased level compared to a control. The control can be any non-infected biological sample or system. Typically, the control is of the same species as the infected biological sample or system. A patient before surgery and/or before the onset of sepsis or another severe infection may, for example, serve as a control. The skilled person in the field of medicine and medical biology will easily be able to identify an appropriate control to which expression levels can be compared. Typically, an elevated amount of DLL1 may be a concentration of DLL1, which is significantly beyond the standard deviation value of the control. According to a preferred embodiment an elevated amount of DLL1 is a concentration, which is two times or in particular three times the standard deviation value of the mean in the control sample. Three times the standard deviation value of the mean in the control sample gives particularly good results.

Alternatively, for the determination of an elevated amount of DLL1 or for diagnosis of a severe infection it is also beneficial to define a cut-off value and to take into account such cut-off value for the diagnosis of sepsis when a patient's sample is tested in line with the invention. A cutoff value will allow differentiation between the groups of patients having a severe infection or not having a severe infection. A reasonable cut-off value for the case the severe infection is sepsis is about 36,331 pg DLL1 protein per ml. A particularly beneficial diagnostic cut-off value for the case where the severe infection is sepsis can be about 29,538 pg DLL1 protein per ml.

The expression level of DLL1 may be measured in any biological sample. The term "biological sample" as used herein comprises the whole of an organism or any part of an organism. Typically, a biological sample is removed from the organism for ex vivo analysis. A biological sample may include single cells and/or cell cultures and/or tissue cultures. Biological samples also include, but are not limited to, tissues, such as epithelial, muscular, connective, and nervous tissue. The biological sample may comprise, for example, whole blood, buffy coat, plasma, serum, peripheral blood mononuclear cells (PBMCS), neutrophils, monocytes, T cells, urine, spinal fluid, lymph fluid, external secretions of the skin, tears, and/or saliva.

In one embodiment of the invention, the expression level of DLL1 is measured from a single cell or a cell culture. The cell or cell culture may comprise cells of the immune system, in particular. Typically, the cell or cell culture comprises an immune cell. Preferably, the cell is a leukocyte. More preferably, the cell is a monocyte. Preferably, the cell culture comprises leukocytes. More preferably, the cell culture comprises monocytes.

In another embodiment, the expression level of DLL1 is measured from a tissue. Preferably, the expression level of DLL1 is measured from a blood sample. The term "blood" as used herein includes whole blood, blood plasma and blood serum. Preferably, the expression level of DLL1 is measured from a blood plasma sample.

In a preferred embodiment, the level of expression of DLL1 is measured and determined from a blood plasma sample taken from a patient. The term "patient" as used herein includes both human and non-human mammals in risk of a severe infection or sepsis. Often, patients are humans or animals that have undergone surgery.

Any appropriate means of measuring protein expression may be used. Typically, protein expression is measured and determined using an immunoassay. Preferably, protein expression is measured and determined using an enzyme-linked immunosorbent assay (ELISA) directed to a specified protein or polypeptide sequence. Protein expression levels may also be measured and determined using an immunoblot assay, such as a Western blot assay, mass spectrometry, ELISpot or flow cytometry and immunohistochemistry.

Any appropriate means of measuring nucleotide expression may be used to measure the expression level of DLL1. For example, expression may be measured by performing microarray analysis, polymerase chain reaction (PCR), reverse transcriptase polymerase chain reaction (RT-PCR), a Northern blot, Southern Blot, or a serial analysis of gene expression (SAGE).

Severe infections are particularly evasive medical conditions, which may result in life-threatening organ failure evoked by a dysregulated immune response to infection. Examples for severe infections are sepsis, pneumonia, and meningitis.

BRIEF DESCRIPTION OF THE DRAWINGS

in FIG. 5B n=50 and in FIG. 5C, Cohort 3: n=100. With references to control patients following extensive visceral surgery ("post-OP"); Cohort 1: FIG. 5A n=30, Cohort 2 and in FIG. 5B n=20. With reference to healthy subjects ("Healthy"); Cohort 1: In FIG. 5A n=30, Cohort 2: and in FIG. 5B n=20 from these three independent clinical studies (Cohort 1 (A), Cohort 2 (B), Cohort 3 (C); see Example 4 for further study details). ***$p \leq 0.0001$; Mann-Whitney U test.

FIG. 7 shows a ROC analysis of DLL-1 protein levels from blood plasma samples (sepsis patients: n=327; controls: n=377) where AUC=area under the curve.

FIGS. 8A and 8B show CD14+ monocytes that were isolated from blood of healthy donors and stimulated with 100 ng/ml LPS or infected with $10^8$ E.coli/$10^6$ monocytes. After two hours bacteria were killed with gentamicin. Control cells (−) were left untreated. The next day cell lysates were produced. For western blot analyses equal amounts of protein lysates were blotted and probed with antibodies against DLL1 or Actin (loading control) (FIG. 8B).

Figure 1:
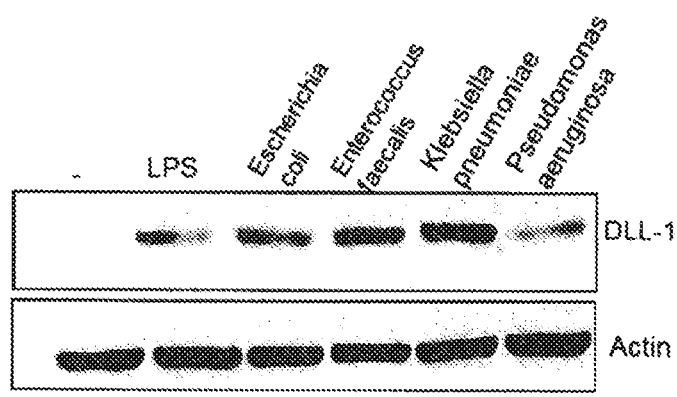
FIG. 1 illustrates a Western blot. $CD14^+$ monocytes were isolated from blood of healthy donors and either infected in vitro with $1 \times 10^6$ bacteria/mL (Escherichia coli, Pseudomonas aeruginosa, Klebsiella pneumoniae, Enterococcus faecalis) or stimulated with 100 ng/mL of lipopolysaccharide (LPS) compared to a control. After two hours, bacteria were killed with gentamicin. Control cells (−) were left untreated. The next day cell lysates were produced. For western blot analyses equal amounts of protein lysates were blotted and probed with antibodies against DLL1 or Actin (loading control).

The following examples serve to further explain the invention, specifically with reference to certain embodiments and figures, which, however, are not intended to limit the present disclosure.hh

EXAMPLES

Example 1

Delta-Like Ligand 1 Detects Bacterial Infection In Vitro

This example checked whether the Notch ligand DLL1 could be upregulated in sepsis patients and therefore could be used as a potential biomarker. An in vitro infection model with sepsis-relevant bacteria was used. In the experimental setup blood-derived monocytes from healthy donors was infected for two hours with different gram negative (Escherichia coli, Pseudomonas aeruginosa, Klebsiella pneumoniae) and gram positive bacteria (*Enterococcus faecalis*) and subsequently bacteria was killed with antibiotics. Furthermore cells were stimulated with TLR4 agonist lipopolysaccharide (LPS), a component of gram negative cell wall which can cause septic shock when circulating in the blood stream. After overnight incubation of infected and LPS-stimulated cells lysates were produced for western blot analysis for the detection of DLL1. The experimental details are explained below.

Cell Isolation and Culture

Peripheral blood-derived mononucleated cells were isolated from fresh blood or buffy coat from healthy donors by means of density gradient centrifugation (Biocoll™ separating solution, 1.077 g/ml, Biochrom AG, Berlin, Germany). Cells were washed three times with PBS and CD14+ magnetically labeled cells were positively selected via the autoMACS™ separator (autoMACS, program: possel, Miltenyi Biotec, Bergisch Gladbach, Germany), supplemented with 100 IU/mL of penicillin, 100 µg/mL streptomycin containing 10% heat inactivated fetal calf serum (FCS, Promocell, Heidelberg, Germany) at 37° C. in a humidified atmosphere in the presence of 5% $CO_2$.

Bacterial Cultures

*Escherichia coli, Pseudomonas aeruginosa, Klebsiella pneumoniae*, and *Enterococcus faecalis* were separately cultured overnight at 37° C. at 5% CO2 in a humidified atmosphere. The next day, one clone from each culture was transferred into Tryptic Soy Broth media and after 2 hours under constant stirring at 37° C., bacterial suspension was adjusted by absorption measurement to a concentration of $10^8$/mL RPMI.

In Vitro Infection $1 \times 10^6$ sorted $CD14^+$ monocytes were plated in a 24-well plate format in 1 mL RPMI/10% FCS. Cells were infected either with $1 \times 10^6$ bacteria/mL or were stimulated with toll-like receptor 4 (TLR4) agonist lipopolysaccharide (100 ng/ml LPS). After two hours 100 ng/mL gentamicin (PAA Laboratories, Inc) was added to the bacterial cultures to kill the bacteria.

After overnight incubation of infected and LPS-stimulated cells, cell lysates were produced and Western Blot analysis was performed using Actin as a control.

Western Blot Assay $2 \times 10^6$ cells were lysed in RIPA lysis buffer containing protease inhibitors (cOmplete™, Roche, Mannheim, Germany) and phosphatase inhibitor (PhosSTOP™, Roche). Cell lysates were then separated by 10% SDS-PAGE and electrotransferred to nitrocellulose membranes (Whatman Protran nitrocellulose membrane; neoLab, Heidelberg, Germany). After blocking (TBS/0.05% Tween-20/5% BSA) and washing (TBS/0.05% Tween) steps, immunoblotting with antibodies against DLL-1 and beta-Actin(Cell Signaling Technology). Detection was enhanced by chemiluminescence (ECL; Perkin Elmer, Groningen, Netherlands).

FIG. 1 shows that delta-like ligand 1 protein is highly detectable in all LPS-stimulated and bacterial infected monocytes but not in control cells. Thus, delta-like ligand 1 protein is suitable for detecting a cellular infection of both gram-positive and gram-negative etiology.

Example 2

Delta-Like Ligand 1 is Upregulated in a Mouse Sepsis Model

As it was seen that activated DLL1 is highly abundant in in vitro bacterial infected monocytes, behaviour of the Notch ligand was examined in a mouse endotoxin sepsis model. LPS (precisely the lipid part of LPS) is also termed endotoxin and commonly used in animal models of sepsis. In critically ill patients, increased concentrations of serum endotoxin have been associated with the development of sepsis, disease severity, and mortality. The theory that endotoxin plays a significant role in the pathogenesis of human sepsis is supported by the observation that antibiotic therapy can lead to a sudden release of massive amounts of endotoxin from dead bacteria and a worsening of the condition. Here 12 weeks old male mice were used for experimental purposes.

Twelve-week old male mice were injected intraperitoneally with either the lipid portion of LPS (n=16) or NaCl (n=15; as a control). After 24 hours, blood was drawn. Cell-free supernatants were harvested and analyzed for levels of mouse delta-like ligand 1 protein using a commercial ELISA assay (abcam) following standard protocol.

Figure 2:
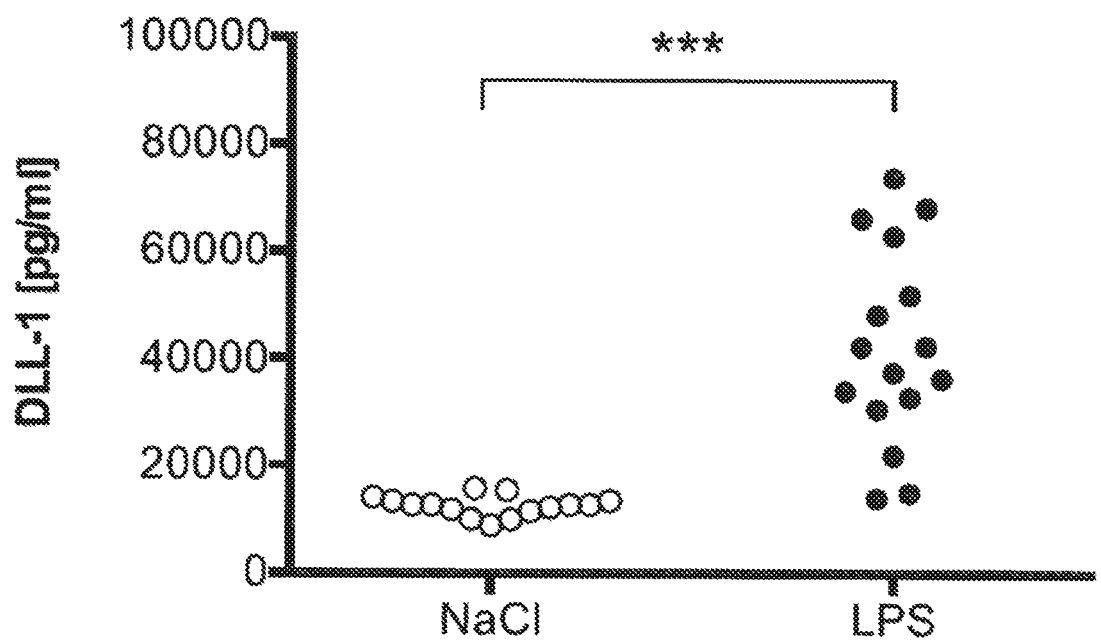
FIG. 2 shows ELISA results from 12-week old mice injected (i.p.) with either LPS (n=16) or NaCl (n=15; control group). Twenty-four hours following injection blood samples were taken and quantification of plasma concentrations were performed by mouse DLL-1 ELISAs ($p \leq 0.0001$; Mann-Whitney U test).

FIG. 2 shows that delta-like ligand 1 protein is elevated in the blood of LPS-infected mice when compared to that of control mice. DLL1 is upregulated in a mouse sepsis model. Thus, delta-like ligand 1 protein is suitable for detecting an infection associated with LPS in the blood of an in vivo animal model of sepsis.

Example 3

Delta-Like Ligand 1 is Upregulated in Sepsis Patients 50 patients were included in the study, all of whom showed signs of severe sepsis following abdominal surgery. Sepsis was defined according to the criteria of the Surviving Sepsis Campaign. Only non-pregnant patients of at least 18 years were included. Further exclusion criteria included autoimmune diseases. After inclusion, blood samples were drawn from septic patients directly following identification of the first signs of sepsis ("t0"), after 24 hours ("t24"), 48 hours ("t48"), and 168 hours ("t168").

20 control patients who had undergone abdominal surgery but presented no signs of sepsis ("OP t2") had their blood drawn 48 hours following surgery. 20 healthy volunteers ("healthy") were recruited as non-operated controls and had their blood drawn once.

Blood plasma was analyzed for the levels of human delta-like ligand 1 protein and additionally human delta-like ligand 4 protein using commercial ELISA assays (DLL1-RayBio®; DLL4-biocat) following standard protocol. Levels of proteins were statistically analyzed using the Mann-Whitney U test.

Figure 3A:
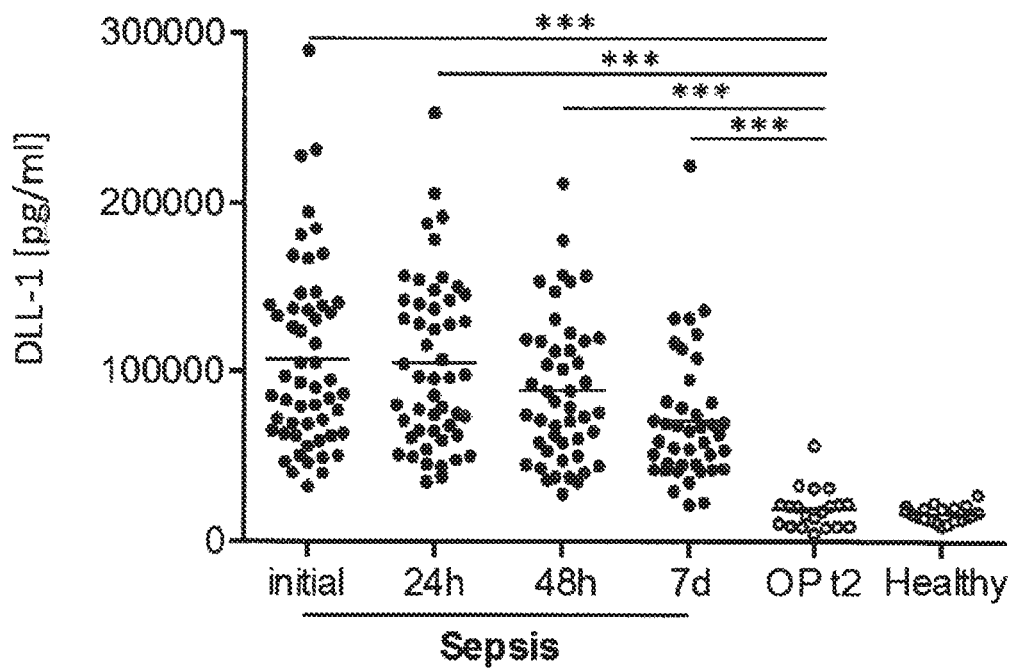
FIGS. 3A and 3B show ELISA analysis of expression levels of (3A) DLL-1 or (3B) DLL-4 from blood plasma samples from sepsis patients (n=50) taken immediately (t0), 24 hours (t24), 48 hours (t48), and 168 hours (t168) following the first identification of sepsis symptoms compared to ELISA results from blood plasma samples from healthy donors (healthy; n=20) and control patients following abdominal surgery (48 h post-OP ("OP t2"; n=20). ***$p \leq 0.0001$; Mann-Whitney U test.

FIG. 3A shows that delta-like ligand 1 protein is elevated in the blood of patients diagnosed with sepsis compared to both healthy controls and patients who underwent abdominal surgery, but who did not show signs of sepsis.

Figure 3B:
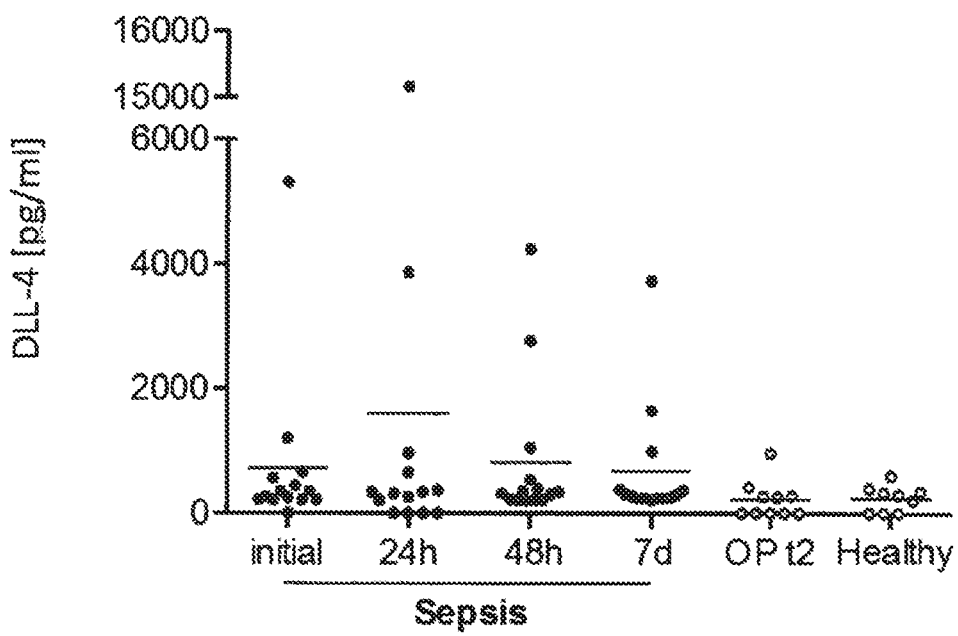

FIG. 3B shows that delta-like ligand 4 protein is not elevated or not significantly elevated in the blood of patients diagnosed with sepsis compared to both healthy controls and non-infected patients who underwent abdominal surgery.

Thus, delta-like ligand 1 protein, but not the closely related delta-like ligand 4 protein, is suitable for detecting the presence of sepsis in the blood of patients following abdominal surgery and for differentiating the infected patients from both healthy controls and non-infected patients.

Figure 4A:
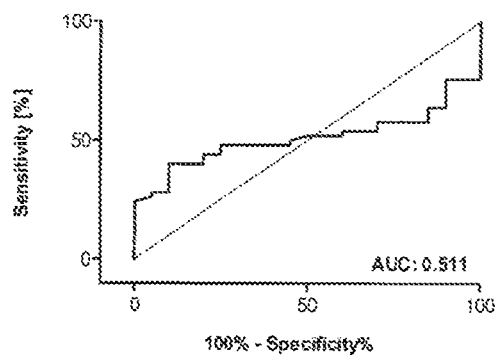
FIGS. 4A-4F show the results of ROC analysis of leukocytes for sepsis patients at t0 versus OPt2 control patients (FIG. 3A); CRP levels of sepsis patients at t0 versus OPt2 control patients (FIG. 3B); DLL-1 levels of sepsis patients at t0 versus OPt2 control patients (FIG. 3C); DLL-1 levels of sepsis patients at t0 versus healthy volunteers (FIG. 3D); DLL-4 levels of sepsis patients at t0 versus OPt2 control patients (FIG. 3E); and DLL-4 levels of sepsis patients at t0 versus healthy volunteers where AUC=area under the curve.
Figure 4B:
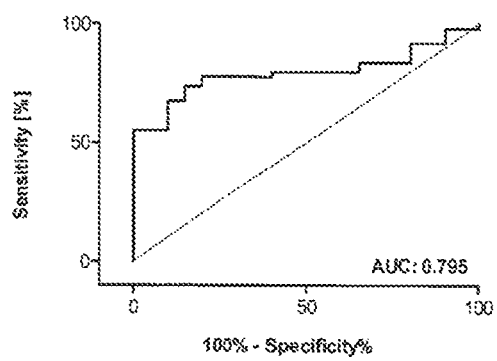
Figure 4C:
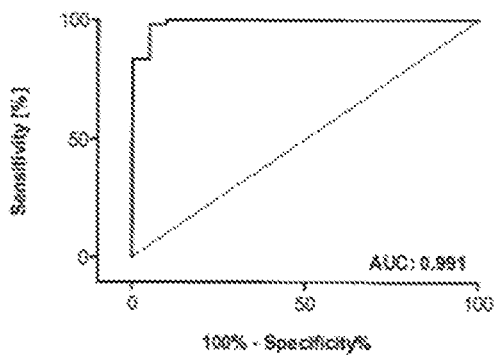
Figure 4D:
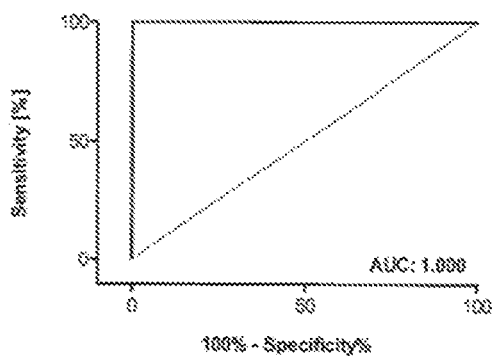
Figure 4E:
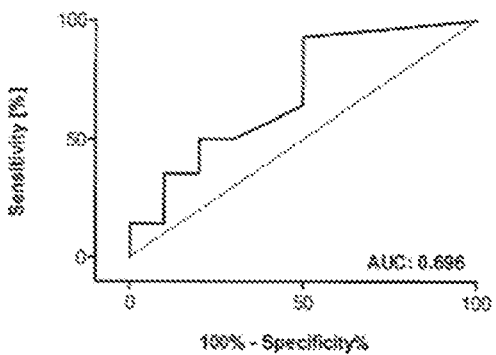
Figure 4F:
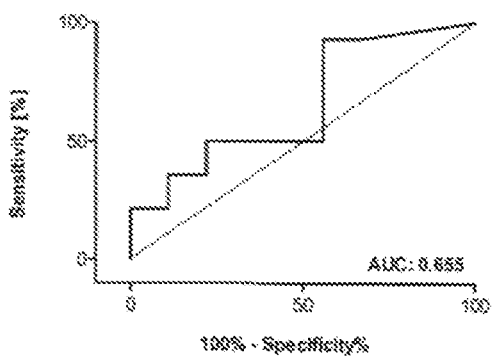

The collected data for delta-like ligand 1 protein and delta-like ligand 4 protein were analyzed using the Receiver Operating Characteristic (ROC) Curve. The area under the ROC curve (AUC) was calculated and the data were compared with the established clinically relevant markers of leukocyte count and CRP. In detail the area under the curve (AUC) of ROC curve t0 versus Op t2 was 0,511 (cutoff 20.73/n1) (FIG. 4A) for leucocytes and 0,795 (cutoff 175.1 mg/ml) for CRP (FIG. 4B). The AUC of DLL1 Sepsis t0 versus OP t2 was 0.991 (cutoff 36,331 pg/ml) and 1.0 (cutoff 25,269 pg/ml) Sepsis t0 versus healthy (FIGS. 4C and 4D). Hence the prediction of infection by DLL-1 is far more reliable than the routinely used biomarkers CRP and leucocyte count. The AUC of the DLL4 ROC analysis was 0,696 (cutoff 1,084 pg/ml) when compared with OP t2 (FIG. 4E) and 0,655 (cutoff 639.3 pg/ml) when compared with healthy controls (FIG. 4F).

Example 4

Delta-Like Ligand 1 is Upregulated in Sepsis Patients

Plasma samples collected within various studies were secondarily analyzed for the concentration of Delta-like ligand 1 (DLL1) by ELISA. Overall, 180 adult patients with sepsis (see "Sepsis" in FIGS. 5A-5C) were analyzed from three independent cohorts as outlined below using the scheme: "[German Clinical Trials Register reference number]/[ethics vote reference number] (responsible committee)":
Cohort 1: [DRKS00012446]/[S-200/2017] (Heidelberg, Germany), n=30 (see FIG. 5A)
Cohort 2: [DRKS00005463]/[S-097/2013] (Heidelberg, Germany), n=50 (see FIG. 5B).
Cohort 3: [DRKS00008090]/[S-247/2014] (Heidelberg, Germany), n=100 (see FIG. 5C).

Samples were taken on the time of study inclusion ("initial) for all three cohorts as well as 24 h ("24 h") and 48 h ("48 h") after study inclusion for cohorts 1 and 2. All patients were recruited either according to the Sepsis-2 (2≥SIRS criteria in combination with a clinically suspected or proven infection; Cohorts 1 and 2) or Sepsis-3 (change in SOFA score of 2≥points and clinically suspected or proven infection; Cohort 3) consensus criteria.

Figure 5A:
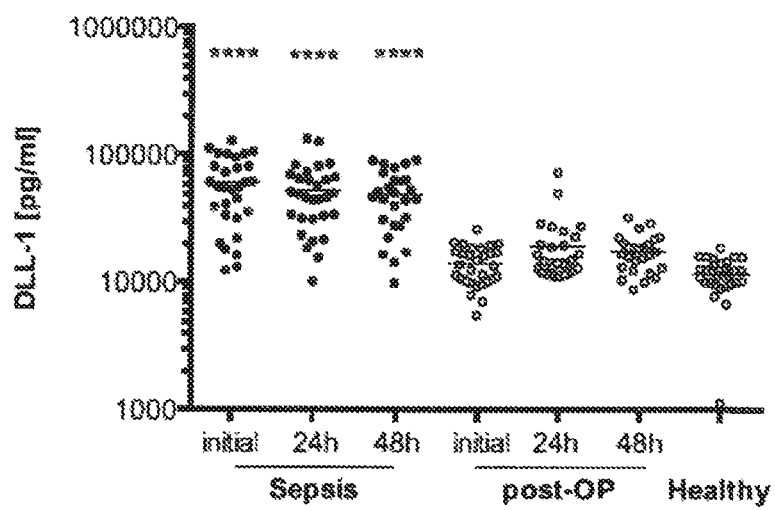
FIGS. 5A-5C show ELISA analysis from three independent clinical studies (Cohorts 1, 2 and 3) of DLL-1 protein levels from blood plasma samples from sepsis patients, post-op patients and healthy individuals. With references to sepsis patients in FIG. 5A ("Sepsis"); Cohort 1: n=30, Cohort 2.
Figure 5B:
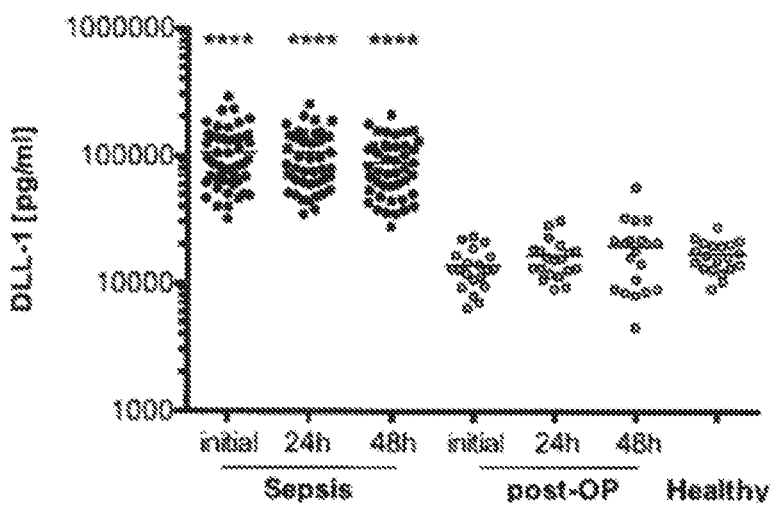
Figure 5C:
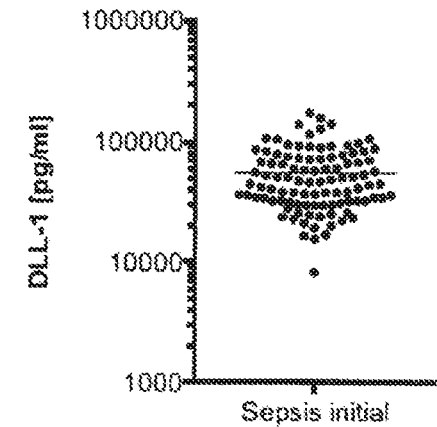

In addition, Cohorts 1 and 2 enrolled patients after extensive visceral surgery who showed no signs of infection at any time point during the study (see "post-OP" in FIGS. 5A-5C; Cohort 1: n=30, Cohort 2: n=20) and healthy volunteers ("Healthy"; Cohort 1: n=30, Cohort 2: n=20).

Cohort 2 corresponds to the same cohort as described under Example 3. Thus, the data values in FIG. 5B are identical to the data values in FIG. 3A.

Figure 6A:
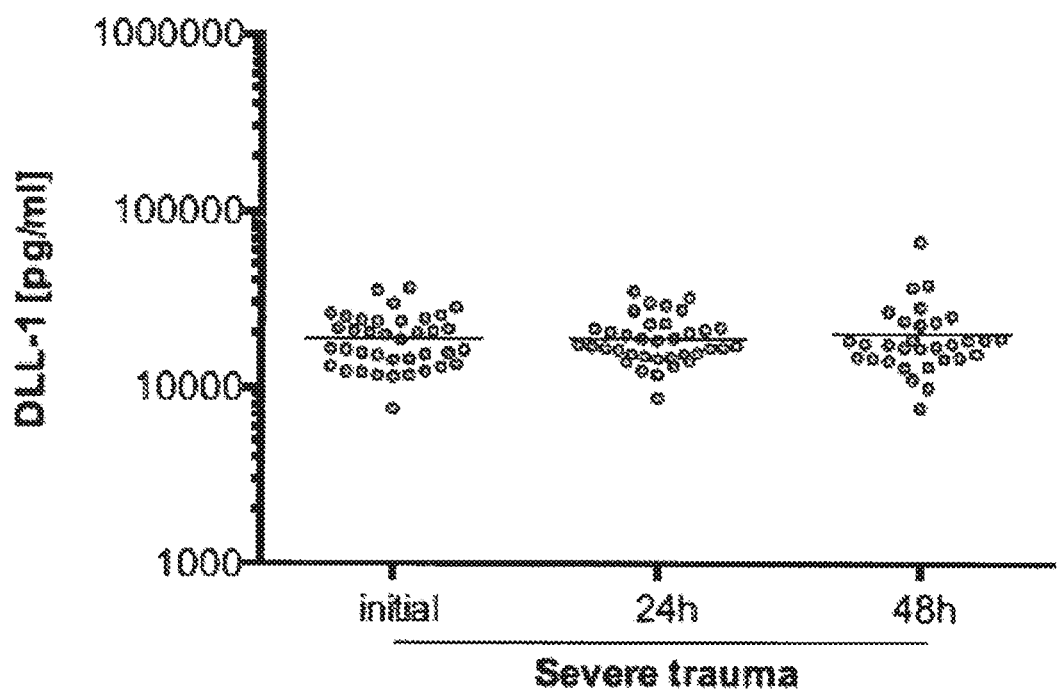
FIG. 6A shows FigELISA analysis of DLL-1 protein levels from blood plasma samples from a group of patients after severe trauma (n=38) taken immediately ("initial"), 24 hours ("24 h") and 48 hours ("48 h") following study inclusion (latest within 24 h after onset of clinical symptoms).
Figure 6B:
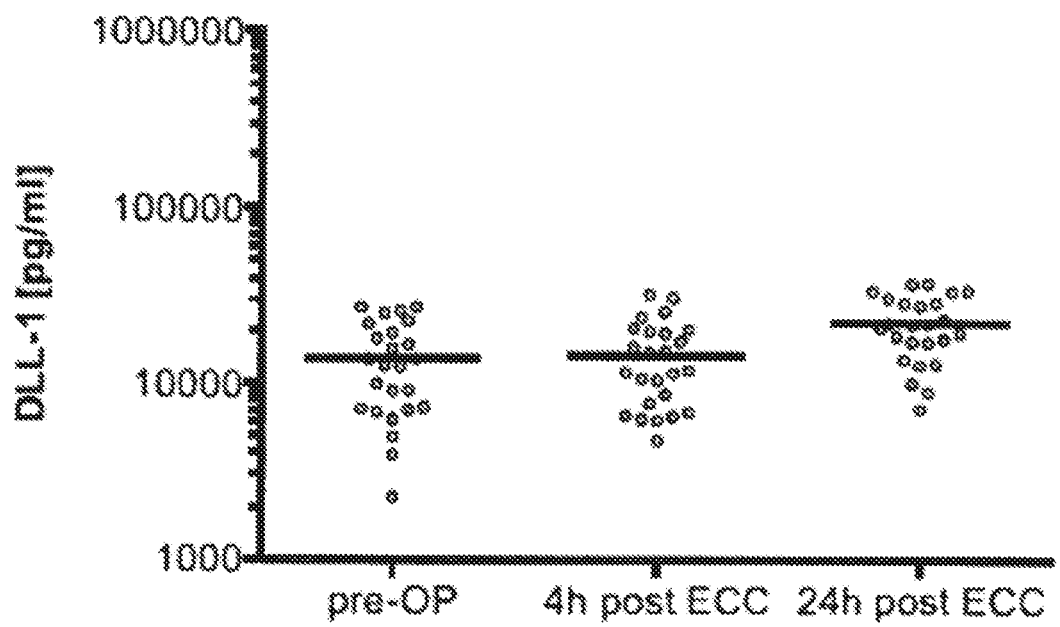
FIG. 6B show ELISA analysis of DLL-1 protein levels from blood plasma samples from patients (n=25) subjected to cardiac surgery under extracorporeal circulation. Protein levels are shown for before surgery ("pre-OP"), 4 hours following extracorporeal circulation ("4 h post ECC"), and 24 hours following extracorporeal circulation ("24 h post ECC"). These patient cohorts showed no signs of infection at any time point.

Further controls included a cohort of 38 patients after severe trauma ([DRKS00010991]/[164/14] (Giessen, Germany); see FIG. 6A) and a cohort of 25 patients subjected to cardiac surgery under extracorporeal circulation ([S-112/2018] (Heidelberg, Germany); see FIG. 6B).

Data analysis was performed with GraphPad Prism (version 6.0, GraphPad Software Inc.). Scatter plots were used for visualization. For group comparisons, non-parametric Mann-Whitney U test was used and a p-value<0.05 was assumed significant; In FIGS. 5A and 5B **** marks p-values<0.0001.

For the evaluation of the diagnostic value of DLL1, all samples from patients with sepsis (all time points, n=327 samples from 180 patients) were combined and compared to all samples of the control group (all time points, n=377 samples; 327 samples from 113 control patients and 50 samples from 50 healthy volunteers) using ROC analysis. The optimal cut-off was calculated by the Youden index procedure ((Sensitivity+Specificity)−100)).

The number of 327 (Sepsis) respectively 377 (Control) samples given above and used in the combined ROC analysis results from patient loss over the observation period (mainly due to death for patients with sepsis and hospital discharge for patients after surgery or severe trauma). Sample numbers are in detail:
Cohort 1
Sepsis: 30/30/27 (initial/24 h/48 h)
Post-OP: 30/29/28 (initial/24 h/48 h)
Healthy: 30
Cohort 2
Sepsis: 50/46/44 (initial/24 h/48 h)
Post-OP: 20/20/20 (initial/24 h/48 h)
Healthy: 20
Cohort 3
Sepsis: 100 (initial)
Severe Trauma
38/36/31 (initial/24 h/48 h)
Cardiac Surgery
25/25/25 (pre-OP/6 h/24 h post ECC)

Initially after recruitment, mean plasma concentrations of patients with sepsis in Cohorts 1, 2 and 3 were 60,292 pg/ml (95% CI: 47,820-72,765; n=30), 106,126 pg/ml (95% CI: 90,102-122,149; n=50) and 56,064 pg/ml (95% CI: 49,494-62,634; n=100), respectively (see FIGS. 5A-5C). Mean plasma concentrations of patients with sepsis in Cohorts 1 and 2 at t=24 h were 53,027 pg/ml (95% CI: 41,824-64,229; n=30) and 104,944 pg/ml (95% CI: 89,786-120,101; n=46), respectively. Mean plasma concentrations of patients with sepsis in Cohorts 1 and 2 at t=48 h were 49,485 pg/ml (95% CI: 39,766-59,205; n=27) and 88,999 pg/ml (95% CI: 75,490-102,508; n=44), respectively. Levels differed highly significant between sepsis patients and controls (i.e. control patients and healthy subjects) at the corresponding time points after surgery.

DLL1 concentrations of the cohorts of control trauma patients (see "post-OP" in FIGS. 5A and 5B and all data in FIG. 6A), as well as patients before and after cardiac surgery (see FIG. 6B), were remarkably lower compared to patients with sepsis at all time points measured.

Mean plasma concentrations of the control surgical patients ("post-OP") in Cohort 1 at t=initial, t=24 h, and t=48 h were 14,193 pg/ml (95% CI: 12,385-16,001; n=30), 19,550 pg/ml (95% CI: 14,536-24,565; n=29), and 17,721 pg/ml (95% CI: 15,498-19,944; n=28), respectively.

Mean plasma concentrations of the control surgical patients ("post-OP") in Cohort 2 at t=initial, t=24 h, and t=48 h were 13,548 pg/ml (95% CI: 11,275-15,821; n=20), 16,187 pg/ml (95% CI: 13,409-18,964; n=20), and 19,287 pg/ml (95% CI: 13,618-24,955; n=20), respectively.

Mean plasma concentrations of the control severe trauma patients in FIG. 6A at t=initial, t=24 h, and t=48 h were 19,119 pg/ml (95% CI: 16,892-21,345; n=38), 19,224 pg/ml (95% CI: 17,184-21,263; n=36), and 20,409 pg/ml (95% CI: 16,351-24,468; n=31), respectively.

Mean plasma concentrations of the control cardiac surgery patients in FIG. 6B at t=initial, t=24 h, and t=48 h were 13,846 pg/ml (95% CI: 10,633-17,059; n=25), 14,603 pg/ml (95% CI: 11,356-17,850; n=25), and 22,194 pg/ml (95% CI: 18,497-25,891; n=25), respectively.

DLL1 concentrations of healthy controls (see "Healthy" in FIGS. 5A and 5B), were remarkably lower compared to patients with sepsis at all time points measured. There were no significant differences between healthy controls and control patients. Mean plasma concentrations of healthy controls measured in Cohorts 1 and 2 were 11.928 pg/ml (95% CI: 10,645-13,211; n=30), and 16,737 pg/ml (95% CI: 14,542-18,932; n=20), respectively.

Receiver-operator curve (ROC) analysis of all available samples grouped to sepsis (n=327) or controls (n=377) yielded an area-under-curve (AUC) of 0.9555 (95% CI: 0.9401-0.9710; see FIG. 7). An optimal diagnostic cut-off of 29,538 pg/ml was found, yielding a sensitivity of 88.7% and specificity of 93.4%.

Example 5

Delta-Like Ligand 1 Cleavage Products Detect Bacterial Infection In Vitro

Upon binding to its receptor the transmembrane protein DLL1 is cleaved. The extracellular domain is released into the environment. The transmembrane (TM) domain and the intracellular (IC) domain (TMIC-DLL1) remain linked inside of the cell. Further cleavage events can release the IC-DLL1 that will migrate to the nucleus. To investigate, whether TMIC-DLL1 can be used to prove infections the cleavage product was detected in in vitro infected primary monocytes by western blot analyses.

Primary monocytes isolated from blood of healthy donors were infected with gram-negative *Escherichia coli* (*E.coli*) or were stimulated with LPS, the main component of Gram negative outer membranes that activates TLR4 signaling. Bacteria were killed by gentamicin 2 h after infection. The next day infected/LPS-treated cells were lysed and analyzed.

Isolation of Primary Human Monocytes

PBMCs were isolated from fresh blood or buffy coat from healthy donors by density gradient centrifugation (Biocoll separating solution, 1.077 g/ml, Biochrom AG, Berlin, Germany). $CD14^+$ cells were magnetically labeled with beads (MiltenyiBiotec) and selected via the autoMACS separator (autoMACS, program: possel, Miltenyi Biotec, Bergisch Gladbach, Germany) twice. Purified monocytes ($1 \times 10^6$ cells/ml) were cultured in RPMI 1640 (Sigma-Aldrich, Taufkirchen, Germany) supplemented with 100 IU/ml of penicillin, 100 µg/ml streptomycin and 10% heat inactivated fetal calf serum (Promocell, Heidelberg, Germany) at 37° C. in a humidified atmosphere in the presence of 5% $CO2$.

Bacterial Cultures

*Escherichia coli* (ATCC25922) were cultured overnight on Columbia blood sheep agar at 37° C. at 5% $CO_2$ in a humidified atmosphere. The next day 1 colony of each culture was transferred into TSB (Tryptic Soy Broth) media and cultured at constant shaking at 200 rpm/37° C. until mid-log phase.

In Vitro Infection $1 \times 10^6$ sorted $CD14^+$ monocytes were plated in 24-well plate format in 1 ml RPMI/10% FCS. Cells were infected with $10^8$ *E.coli*/$10^6$ monocytes. After 2 h gentamicin was added to a final concentration of 100 ng/ml to kill the bacteria. The next day cells were lysed analyzed.

Western Blot Assay $2 \times 10^6$ cells were harvested and washed with PBS. For whole cell lysates monocytes were lysed in 50 µl RIPA buffer (50 mM Tris-HCl, pH7.4; 1% Igepal; 0.25% sodium deoxycholate; 150 mM NaCl; 1 mM EDTA; 1 mM PMSF; 1 mg/ml each aprotinin, leupeptin, and pepstatin; 1 mM $Na3VO4$; and 1 mM NaF). Samples were vortexed and incubated 30 min on ice. Lysates were then cleared via centrifugation at 14,000×g for 20 min. Equal amounts of lysates were used for separation by SDS-PAGE (12.5%). After semi-dry transfer onto nitrocellulose membranes (Whatman Protran nitrocellulose membrane; neoLab, Heidelberg, Germany), the latter were blocked with 5% (w/v) BSA in TBS/0.1% (v/v) Tween-20 for 2 h at RT. Probing was performed with antibodies: anti-DLL1, anti-β actin (Cell Signaling Technology, Danvers, Mass., USA) Detection was based on enhanced chemiluminescence (ECL; Perkin Elmer, Groningen, Netherlands).

FIGS. 8A and 8B show that TMIC (transmembrane domain linked to intracellular domain) cleavage product of the delta-like ligand 1 protein is highly detectable in LPS-stimulated and *E. coli* infected monocytes, but not in control cells. Thus, transmembrane domain and intracellular domain DLL1 cleavage products are suitable for detecting an infection, in particular that of gram-negative etiology.

The invention claimed is:

1. A process for analyzing for sepsis in an individual comprising determining the presence of delta-like ligand 1 protein or a nucleotide sequence coding for delta-like ligand 1 protein as a biomarker in an in vitro biological sample, said sepsis determined by observing an expression level of the delta-like ligand 1 protein or the nucleotide sequence coding for delta-like ligand 1 protein in said biological sample.

2. The process of claim 1, wherein the delta-like ligand 1 protein is encoded by the nucleotide sequence SEQ ID NO: 1.

3. The process of claim 1, wherein the delta-like ligand 1 protein is a protein having at least 90% identity with the amino acid sequence of SEQ ID NOs: 2 and/or 3.

4. The process of claim 1, wherein the delta-like ligand 1 protein is a cleavage product of the delta-like ligand 1 protein.

5. The process of claim 4 wherein the delta-like ligand 1 protein is a cleavage product of the delta-like ligand 1 having an amino acid sequence of SEQ ID NO: 4, SEQ ID NO: 5, SEQ ID NO: 6 and/or SEQ ID NO: 7.

6. The process of claim 1, wherein an elevated level of expression of delta-like ligand 1 protein or the nucleotide sequence encoding delta-like ligand 1 protein as compared to a healthy control or a control patient is indicative for the diagnosis of sepsis.

7. The process of claim 6, wherein the level of expression is determined in a biological sample taken from a patient following a surgery.

8. The process of claim 7 wherein the level of expression is determined in a biological sample taken from a patient after an abdominal surgery.

9. The process of claim 1, wherein the biological sample is selected from the group consisting of whole blood, buffy coat, plasma, serum, peripheral blood mononucleated cells (PBMCS), neutrophils, monocytes, T cells, urine, spinal fluid, lymph fluid, external secretions of the skin, tears, and/or saliva.

10. The process of claim 1 wherein information obtained from the in vitro diagnosis is used as guidance for delivery of antibiotic therapy.

11. A method for in vitro diagnosis of sepsis comprising determining the expression level of delta-like ligand 1 protein or a nucleotide sequence coding for delta-like ligand 1 protein in a biological sample and diagnosing sepsis when an elevated level of expression of delta-like ligand 1 protein or a nucleotide sequence coding for delta-like ligand 1 protein when compared to a reference expression level is determined.

12. The method according to claim 11, wherein the delta-like ligand 1 protein is encoded by the nucleotide sequence SEQ ID NO: 1 or a nucleotide sequence being at least 80% identical to SEQ ID NO: 1.

13. The method according to claim 11, wherein the delta-like ligand 1 protein has an amino acid sequence that is at least 90% identical to SEQ ID NOs: 2 or 3, and/or has an amino acid sequence of SEQ ID NO: 4, SEQ ID NO: 5, SEQ ID NO: 6 and/or SEQ ID NO: 7.

14. The method according to claim 11, wherein the biological sample is selected from the group consisting of whole blood, buffy coat, plasma, serum, peripheral blood mononucleated cells (PBMCS), neutrophils, monocytes, T cells, urine, spinal fluid, lymph fluid, external secretions of the skin, tears, and/or saliva.

15. The method according to claim 11, wherein the level of expression is determined in a biological sample taken from a patient following a surgery.

16. The method according to claim 15, wherein the level of expression is determined in a biological sample taken from a patient after an abdominal surgery.

* * * * *